US012721810B2

(12) United States Patent
Meyer

(10) Patent No.: US 12,721,810 B2
(45) **Date of Patent: *Sep. 1, 2026**

(54) AQUEOUS OPHTHALMIC SOLUTIONS OF PHENTOLAMINE AND MEDICAL USES THEREOF

(71) Applicant: Opus Genetics, Inc., Durham, NC (US)

(72) Inventor: Alan Meyer, North Riverside, IL (US)

(73) Assignee: Opus Genetics, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/190,234

(22) Filed: Apr. 25, 2025

(65) Prior Publication Data

US 2025/0262149 A1 Aug. 21, 2025

Related U.S. Application Data

(63) Continuation of application No. 18/538,502, filed on Dec. 13, 2023, now Pat. No. 12,350,366, which is a continuation of application No. 17/401,604, filed on Aug. 13, 2021, now Pat. No. 11,844,858, which is a continuation of application No. 16/398,536, filed on Apr. 30, 2019, now Pat. No. 11,090,261, which is a continuation of application No. 15/783,160, filed on Oct. 13, 2017, now Pat. No. 10,278,918, which is a (Continued)

(51) Int. Cl.
*A61K 9/00* (2006.01)
*A61K 31/417* (2006.01)

(52) U.S. Cl.
CPC .......... *A61K 9/0048* (2013.01); *A61K 31/417* (2013.01)

(58) Field of Classification Search
CPC ............................ A61K 9/0048; A61K 31/417
See application file for complete search history.

(56) References Cited

U.S. PATENT DOCUMENTS 4,443,441 A 4/1984 Galin
4,508,715 A 4/1985 Booth et al.
4,515,295 A 5/1985 Dougherty
(Continued)

FOREIGN PATENT DOCUMENTS

CA 2780043 A1 5/2011
EP 0258865 A2 3/1988
(Continued)

OTHER PUBLICATIONS

Abad et al., "Comparison of Astigmatism Correction Using Shorter Arc Length 90° / 120° Asymmetric Intacs Severe Keratoconus Versus 150° Single-Segment Intacs Severe Keratoconus in Asymmetric Keratoconus," Cornea, (2011), vol. 30, No. 11, pp. 1201-1206.

(Continued)

*Primary Examiner* — Jianfeng Song
(74) *Attorney, Agent, or Firm* — Morgan, Lewis & Bockius LLP

(57) ABSTRACT

The invention provides aqueous ophthalmic solutions of phentolamine or pharmaceutically acceptable salts thereof, medical kits, and methods for using such ophthalmic solutions to improve visual performance in a patient. Exemplary aqueous ophthalmic solutions include those containing phentolamine mesylate, mannitol, sodium acetate, and water.

30 Claims, 15 Drawing Sheets

Related U.S. Application Data continuation of application No. 14/169,339, filed on Jan. 31, 2014, now Pat. No. 9,795,560.

(60) Provisional application No. 61/759,530, filed on Feb. 1, 2013.

(56) References Cited

U.S. PATENT DOCUMENTS 4,629,456 A 12/1986 Edwards
4,659,714 A 4/1987 Watt-Smith
4,834,727 A 5/1989 Cope
4,888,344 A 12/1989 Sunagawa et al.
4,906,613 A 3/1990 Watkins
4,938,970 A 7/1990 Hustead et al.
5,032,392 A 7/1991 Varma
5,059,188 A 10/1991 Goddard
5,134,124 A 7/1992 Nisato et al.
5,149,320 A 9/1992 Dhaliwal et al.
5,192,527 A 3/1993 Abrahmsohn
5,261,903 A 11/1993 Dhaliwal et al.
5,281,591 A 1/1994 Burke
5,288,759 A 2/1994 DeSantis, Jr.
5,494,937 A 2/1996 Asgharian et al.
5,514,118 A 5/1996 Kummer et al.
5,584,823 A 12/1996 Valberg
5,591,426 A 1/1997 Dabrowski et al.
5,627,611 A 5/1997 Scheiner
5,792,767 A 8/1998 Meyer et al.
5,885,550 A 3/1999 Vallier
5,891,882 A 4/1999 Meyer et al.
5,891,913 A 4/1999 Sallmann et al.
5,895,654 A 4/1999 Hartford et al.
6,001,845 A 12/1999 Estok
6,025,396 A 2/2000 Kim et al.
6,043,224 A 3/2000 Lee et al.
6,046,207 A 4/2000 Meyer et al.
6,051,594 A 4/2000 Lowrey
6,106,866 A 8/2000 Ranney
6,291,498 B1 9/2001 Horn
6,420,407 B1 7/2002 Horn
6,432,401 B2 8/2002 Weber et al.
6,515,006 B2 2/2003 Horn
6,638,537 B2 10/2003 Dennis et al.
6,730,065 B1 5/2004 Horn
6,730,691 B1 5/2004 Galin
6,764,678 B2 7/2004 Weber et al.
6,872,390 B2 3/2005 Weber et al.
7,229,630 B2 6/2007 Chen et al.
7,569,230 B2 8/2009 Chen et al.
7,575,757 B2 8/2009 Chen et al.
7,868,035 B2 1/2011 Woodward et al.
8,445,526 B2 5/2013 Horn
8,580,787 B2 11/2013 Horn
8,597,629 B1 12/2013 Horn
8,889,112 B2 11/2014 Horn
8,979,809 B2 3/2015 Horn
9,089,560 B2 7/2015 Meyer
9,789,088 B2 10/2017 Meyer
9,795,560 B2 10/2017 Meyer
10,278,918 B2 5/2019 Meyer
10,772,829 B2 9/2020 Meyer
11,000,509 B2 5/2021 Meyer
11,090,261 B2 8/2021 Meyer
11,717,510 B2 8/2023 Meyer
11,844,858 B2 12/2023 Meyer
12,350,366 B2 7/2025 Meyer
2002/0082288 A1 6/2002 Horn
2002/0183356 A1 12/2002 Weber et al.
2002/0183396 A1 12/2002 Weber et al.
2002/0187986 A1 12/2002 Horn
2003/0203034 A1 10/2003 Huth
2003/0236306 A1 12/2003 Chen et al.
2004/0053894 A1* 3/2004 Mazess .................. A61P 31/04 514/167
2004/0176408 A1 9/2004 Horn
2005/0080056 A1 4/2005 Horn
2005/0181017 A1 8/2005 Hughes et al.
2005/0203099 A1 9/2005 Chen et al.
2006/0211753 A1 9/2006 Horn
2006/0257388 A1 11/2006 Knowles
2007/0049640 A1 3/2007 Pavliv
2007/0098748 A1 5/2007 Chen et al.
2008/0199537 A1 8/2008 Bhagat et al.
2009/0131303 A1* 5/2009 Hong .................. A61K 38/014 514/54
2009/0220618 A1* 9/2009 Xia ..................... A61K 9/0048 424/616
2009/0232763 A1 9/2009 Kabra et al.
2010/0029663 A1 2/2010 Horn
2010/0143419 A1 6/2010 McAffer et al.
2010/0324031 A1 12/2010 Kabra
2011/0178147 A1* 7/2011 Likitlersuang ....... A61K 9/0048 514/401
2012/0136072 A1* 5/2012 Mosher .................. A61K 45/06 514/778
2012/0149748 A1 6/2012 Shanler et al.
2012/0208858 A1 8/2012 Shanler et al.
2012/0238615 A1 9/2012 Chow et al.
2012/0277239 A1 11/2012 Horn et al.
2013/0029919 A1 1/2013 Gore et al.
2013/0143938 A1 6/2013 Horn
2013/0172357 A1 7/2013 Horn
2014/0221445 A1 8/2014 Meyer
2014/0221446 A1 8/2014 Meyer
2016/0051515 A1 2/2016 Meyer
2018/0221274 A1 8/2018 Meyer
2018/0221340 A1 8/2018 Meyer
2019/0254963 A1 8/2019 Meyer
2024/0050412 A1 2/2024 Meyer
2025/0248930 A1 8/2025 Meyer
2025/0248931 A1 8/2025 Meyer

FOREIGN PATENT DOCUMENTS

WO WO-1995005188 A1 2/1995
WO WO-2001085171 A1 11/2001
WO WO-2004000219 A2 * 12/2003 ................ A61P 9/00
WO WO-2005123093 A2 12/2005
WO WO-2007008666 A2 1/2007
WO WO-2009111418 A2 9/2009
WO WO-2011050018 A1 4/2011
WO WO-2011050030 A1 4/2011
WO WO-2011127196 A1 10/2011
WO WO-2012075319 A2 6/2012
WO WO-2012112566 A1 8/2012
WO WO-2012119059 A1 9/2012
WO WO-2012119070 A2 9/2012
WO WO-2013071138 A1 5/2013
WO WO-2013078554 A1 6/2013
WO WO-2013115844 A1 8/2013
WO WO-2013130577 A2 9/2013

OTHER PUBLICATIONS

ACETADOTE® Prescribing Information.

ACULAR® Prescribing Information.

Asa, "K-max Plus", retrieved from http://califasainc.com/pdf/Kmax_Analysis.pdf on May 29, 2016.

BETAGAN® Prescribing Information.

Benson et al., "Is Phentolamine Stable in Solution with Papaverine," The Journal of Urology, (1988), vol. 140, pp. 970-971.

CLARINEX® Prescribing Information.

Hadzija et al., "Physicochemical Stability of Papaverine Hydrochloride-Phentolamine Mesylate Mixtures Used for Intracavernous Injection: A Preliminary Evaluation," The Journal of Urology, (1988), vol. 140, pp. 64-65.

International Search Report and Written Opinion of the International Searching Authority, the U.S. Patent & Trademark Office, for International Application No. PCT/US2014/014067, dated May 21, 2014, 8 pages.

(56) References Cited

OTHER PUBLICATIONS

International Search Report and Written Opinion of the International Searching Authority, the U.S. Patent & Trademark Office, for International Application No. PCT/US2014/014070, dated Apr. 15, 2014, 10 pages.
Martell, A.E. "Chelates of Ascorbic Acid Formation and Catalytic Properties," Advances in Chemistry, vol. 200, pp. 153-187 (1982).
MUCOMYST® Prescribing Information.
OraVerse (phentolamine mesylate) Injection, Prescribing Information, 2 pages.
Safety Data Sheet for D-mannitol, by CCI (year 2012).
Safety Data Sheet for glycerol, by CCI (year 2012).
Soli et al., "Vasoactive Cocktails for Erectile Dysfunction: Chemical Stability of PGE1, Papaverine and Phentolamine," The Journal of Urology, (1998), vol. 160, pp. 551-555.
Troy et al., "Remington: The Science and Practice of Pharmacy", 21st ed., University of the Sciences, Philadelphia, Pennsylvania, 2006, p. 1032.
Tu et al., "Stability of papaverine hydrochloride and phentolamine mesylate in injectable mixtures," American Journal of Hospital Pharmacy, (1987), vol. 44, pp. 2524-2527.
Wang et al., "Degradation Kinetics of Phentolamine Hydrochloride in Solution," Journal of Pharmaceutical Sciences, (1988), Vo. 77, No. 11, pp. 972-976.
Vivacy, "Stylage", retrieved from http://www.stylage.eu/technology.html on May 27, 2016.
Abelson, et al., A. "The Truth about Tachyphylaxis", Review of Ophthalmology, (2006), vol. 13, No. 3, pp. 112-115.
Johnston, C. "Relief for Patients Troubled by Night-Vision Complaints: Presented at AAO", PeerVoice Publication, dated Oct. 21, 2010.
Murphy et al., "How red is white eye? Clinical grading of normal conjunctival hyperemia", May 2007, Eye, vol. 21, No. 4, pp. 633-638.
National Institutes of Health, "Visual acuity test", Feb. 23, 2015, online://medlineplus.gov/ency/article/003396.htm, 3 pages.
European Search Report dated Jun. 21, 2016 from European Patent Application 14746208.9 (6 pages).
Examination Report dated Jan. 31, 2018 from European Patent Application 14746208.9 (6 pages).
Notice of Intention to Grant a Patent dated Apr. 10, 2019 from European Patent Application 14746208.9 (162 pages).
Baudouin et al., "Preservatives in eyedrops: the good, the bad and the ugly," Prog Retin Eye Res. 2010(4):312-34.
Epstein et al. "Comparative Toxicity of Preservatives on Immortalized Corneal and Conjuctival Epithelial Cells," J Ocul Pharmacol Ther. 2009(2):113-9.
Kahook et al., "Comparison of corneal and conjunctival changes after dosing of travoprost preserved with sofZia, latanoprost with 0.02% benzalkonium chloride, and preservative-free artificial tears," Cornea. 2008(3):339-43.
McDonald, "Phentolamine Mesylate Treatment of Severe Night-Vision Complaints" ASCRS Meeting Presentation (dated May 2011).
Ocularis Pharma Presentation (dated Jul. 12, 2009).
2007 Report of the International Dry Eye WorkShop (DEWS), Ocular Surface 2007; 5(2).
Wilcox et al., "Comparison of the effects on pupil size and accommodation of three regimens of topical dapiprazole," Br J Ophthalmol. 1995(79):544-8.
ANDA Notice Letter for RYZUMVI dated Jan. 31, 2025.
McDonald, M.B et al., "Phentolamine Mesylate Treatment of Severe Night Vision Complaints," AAO Abstracts, PO433 (2010).
S. P. Epstein et al., "Toxicity of Ocular Preservatives and Buffering Agents on the Ocular Surface (Corneal and Conjunctival Epithelium)," ARVO Annual Meeting, May 2006.
Bernard E. McCarey et al., "Effect of tear lubricating solutions on in vivo corneal epithelial permeability," Current Eye Research, 16:44-50 (1997).
John L. Ubels, et al., "Artificial tear solutions and protection of the corneal epithelium from desiccation," Journal of Toxicology, vol. 21, No. 4, pp. 273-281 (2002).
Kenneth C. Waterman et al., "Stabilization of Pharmaceuticals to Oxidative Degradation," Pharmaceutical Development and Technology, 7:1, pp. 1-32 (2002).
Pharmaceutical Manufacturing Handbook, Production and Processes, published by John Wiley & Sons, Inc., Hoboken, New Jersey (2008).
Guidance for Industry, Container Closure Systems for Packaging Human Drugs and Biologics, published in May 1999 by the U.S. Department of Health and Human Services, the Food and Drug Administration.
M. R. Bhalekar et al., "Improvement of Photostability in Formulation: A Review," Asian Journal of Chemistry, vol. 20, No. 7, pp. 5095-5108 (2008).
Chapter 8, titled "Formulation and stability of solutions," in Sterile Drug Products, by Michael J. Akers (2010).
Allen C. Templeton and Robert A. Reed, "Headspace Oxygen Analysis in Pharmaceutical Products," in Encyclopedia of Pharmaceutical Technology, pp. 1967-1976 (2007).
A. Amin et al., "Formulation Development for Sterile Liquid Products in Blow-Fill-Seal Packs," Pharmaceutical Technology, pp. 142-154 (2006).
Marguerite A. Constant and Bernard Becker, "The Effects of Vasopressin, Chlorpromazine, and Phentolamine Methanesulfonate," A.M.A. Archives of Ophthalmology, Experimental Tonography, pp. 19-25 (1956).
K. E. Eakins et al., "The action of sympathomimetic amines on the outflow of aqueous humor from the eye," British Journal of Pharmacology, vol. 23, pp. 374-382 (1964).
David L. Murray et al., "Alpha-Adrenergic Receptors in Rabbit Eyes," Journal of Ocular Pharmacology, vol. 1, No. 1, pp. 3-18 (1985).
Yongxin Yu, et al., "$\alpha$1A-Adrenoceptors Mediate Sympathetically Evoked Pupillary Dilation in Rats," Journal of Pharmacology and Experimental Therapeutics, vol. 300, No. 2, pp. 521-525 (2002).
Yongxin Yu, et al., "Studies of a-Adrenoceptor Antagonists on Sympathetic Mydriasis in Rabbits," Journal of Ocular Pharmacology and Therapeutics, vol. 19, No. 3, pp. 255-263 (2003).
Marguerite B. McDonald, "Phentolamine Mesylate Treatment of Severe Night Vision Complaints," The Annual Meeting of the American Academy of Ophthalmology, Oct. 2010.
Marguerite McDonald, "Phentolamine Mesylate Treatment of Severe Night-Vision Complaints," the American Society of Cataract and Refractive Surgery ("ASCRS") and the American Society of Ophthalmic Administrators ("ASOA") Symposium & Congress in Mar. 2011 in San Diego.
Chapter 24, titled "Drugs and the Eye," in Common Eye Disease and their Management, Third Edition, published by Springer-Verlag London Limited in 2006.
Chapter 8, titled "Mydriatics and Mydriolytics," in "Clinical Ocular Pharmacology," Fifth Ed., published by Elsevier Ltd. in 2008.
Chapter 7, titled "Diagnostic Drugs," in "Optometry: Science, Techniques and Clinical Management," published by Elsevier Ltd. in 2009.
Chapter 9, titled "Iris and Ciliary Body," in "Fundamentals and Principles of Ophthalmology," Basic and Clinical Science Course, Section 2, 2010-2011, published by the American Academy of Ophthalmology in 2010.
Tammy S. Hogan et al., "Dose-Response Study of Dapiprazole HCl in the Reversal of Mydriasis Induced by 2.5% Phenylephrine," Journal of Ocular Pharmacology and Therapeutics, vol. 13, No. 4, pp. 297-302 (1997).
NCT01703559, clinical study report titled "The Safety and Efficacy of Phentolamine Mesylate Ophthalmic Solution in Subjects With Severe Night Vision Complaints," submitted to the ClinicalTrials.gov on Oct. 9, 2012.
Mary Tavares et al., "Reversal of soft-tissue local anesthesia with phentolamine mesylate in pediatric patients," Journal of American Dental Association, 139(8):1095-1104 (2008).
The prescribing information for OraVerse (phentolamine mesylate) Injection, Mar. 2008.

(56) References Cited

OTHER PUBLICATIONS

David H. McDougal and Paul D. Gamlin, "Autonomic Control of the Eye," Comprehensive Physiology, vol. 5, pp. 439-473 (2015).
Daniel B. Moore et al., "An objective assessment of the variability in number of drops per bottle of glaucoma medication," BMC Ophthalmology, 17:78 (2017).

* cited by examiner

Figure 3D

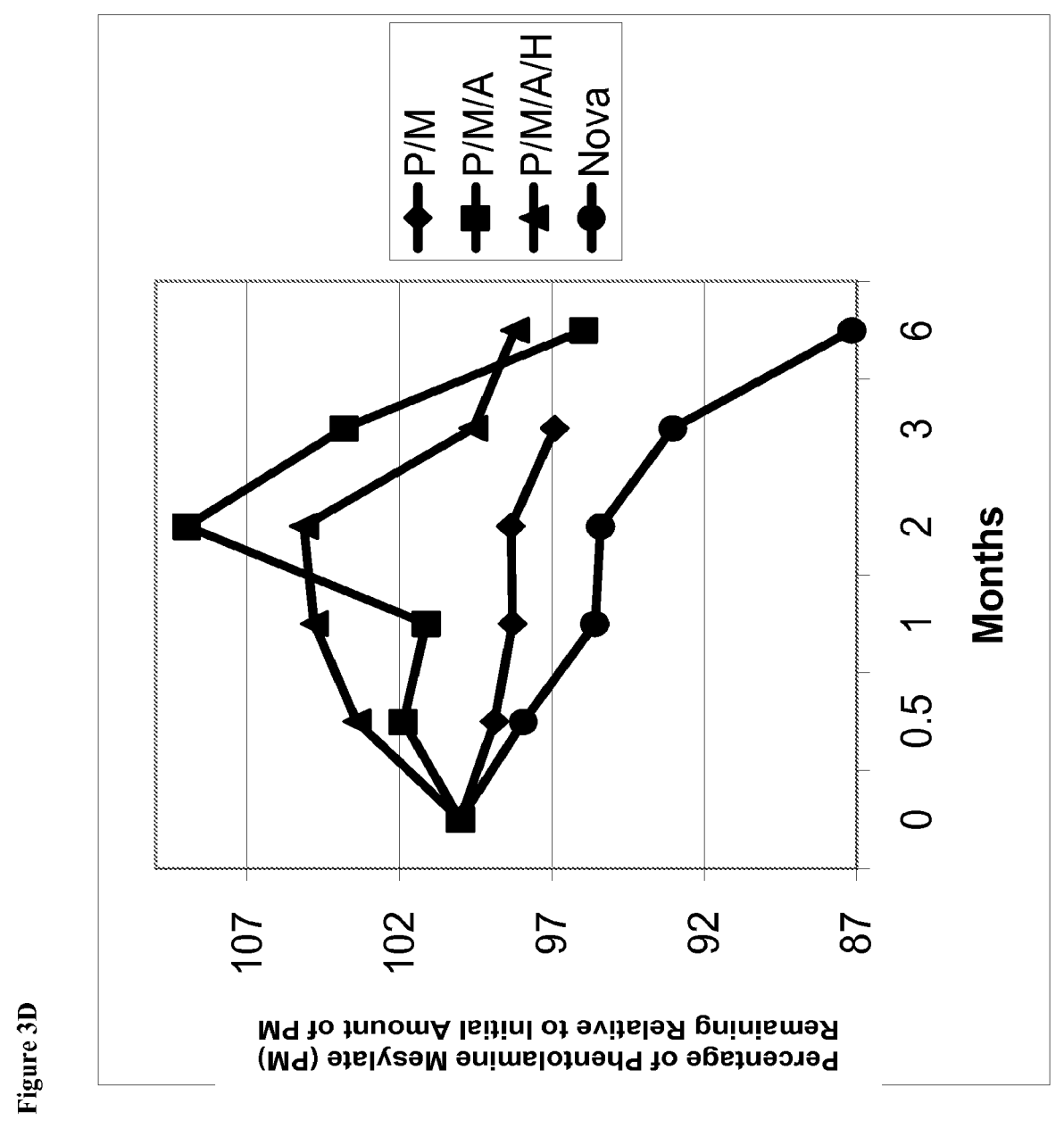

Percentage of Phentolamine Mesylate (PM) Remaining Relative to Initial Amount of PM 107
102
97
92
87

0
0.5
1
2
3
6

Months

P/M
P/M/A
P/M/A/H
Nova

AQUEOUS OPHTHALMIC SOLUTIONS OF PHENTOLAMINE AND MEDICAL USES THEREOF

RELATED APPLICATIONS

This application is a continuation of U.S. patent application Ser. No. 18/538,502, filed Dec. 13, 2023, which is a continuation of U.S. patent application Ser. No. 17/401,604, filed Aug. 13, 2021, now U.S. Pat. No. 11,844,858, which is a continuation of U.S. patent application Ser. No. 16/398,536, filed Apr. 30, 2019, now U.S. Pat. No. 11,090,261, which is a continuation of U.S. patent application Ser. No. 15/783,160, filed Oct. 13, 2017, now U.S. Pat. No. 10,278,918, which is a continuation of U.S. patent application Ser. No. 14/169,339, filed Jan. 31, 2014, now U.S. Pat. No. 9,795,560, which claims the benefit of and priority to U.S. Provisional Patent Application Ser. No. 61/759,530, filed Feb. 1, 2013; the contents of each application are hereby incorporated by reference in their entirety.

FIELD OF THE INVENTION

The invention relates to aqueous ophthalmic solutions of phentolamine or pharmaceutically acceptable salts thereof, medical kits, and methods for using such solutions to improve visual performance in a patient.

BACKGROUND

Deficient visual performance can have a significant negative impact on a patient's quality of life, affecting, for example, ability to perform normal daily tasks, perform at school, and perform at work. One type of vision problem experienced by a substantial number of patients is poor night vision. The inability to see clearly under such low light conditions can make it difficult and/or dangerous for a patient to operate a motor vehicle at nighttime. Patients that are more likely to experience night vision problems include those suffering from night myopia, those with an equatorial cortical cataract, and those who have had surgery to insert an intraocular lens and/or underwent LASIK surgery. Exemplary symptoms of poor night vision include glare, halos, starburst, ghosting patterns, and/or poor depth perception.

Certain therapies have been described for improving visual performance. For example, the Bernstein Center for Visual Performance offers programs that utilize visual aids, such as puzzles, stereoscopes, and eye glasses, designed to improve visual performance. U.S. Pat. Nos. 6,730,065; 6,515,006; 6,420,407; and 6,291,498 describe the use of phentolamine to, for example, optimize pupil size in a patient. However, the need exists for additional compositions and methods that provide improvement in visual performance.

Despite this need, it is difficult to prepare stable, aqueous formulations of phentolamine salt forms without the use of a chelating agent, such as, disodium ethylenediaminetetraacetic acid (EDTA). U.S. Pat. No. 7,229,630 describes test results of various aqueous formulations containing phentolamine mesylate and states, for example, that the presence of a metal chelator is believed to be necessary to maintain stability of the formulation.

In view of the need for better formulations for administering phentolamine or a pharmaceutically acceptable salt thereof to the eye of a patient, research has been performed and the present patent application describes the surprising discovery of stable, aqueous ophthalmic solutions free of a chelating agent. The aqueous ophthalmic solutions free of a chelating agent can be used to administer phentolamine mesylate to the eye of a patient, and the aqueous ophthalmic solutions have demonstrated good stability upon storage.

Accordingly, the present invention addresses the aforementioned need for improved formulations that can be administered to the eye of a patient for improving visual performance, and the invention provides other related advantages.

SUMMARY

The invention provides aqueous ophthalmic solutions of phentolamine or pharmaceutically acceptable salts thereof, medical kits, and methods for using such solutions to improve visual performance in a patient. One of the benefits of the aqueous ophthalmic solutions is they have surprisingly been found to be stable to extended storage, even though they do not have a chelating agent. Another benefit of the aqueous ophthalmic solutions is that they are well-suited for administration to the eye of a patient in the form of an eye drop. For example, the aqueous ophthalmic solutions avoid or minimize any burning or stinging sensation often associated with certain phentolamine mesylate solutions described in the literature. Various aspects and embodiments of the invention are described in further detail below.

Accordingly, one aspect of the invention provides an aqueous ophthalmic solution free of a chelating agent, comprising: (a) about 0.1% (w/v) to about 4% (w/v) of phentolamine or a pharmaceutically acceptable salt thereof, (b) about 1% (w/v) to about 6% (w/v) of at least one polyol compound having a molecular weight less than 250 g/mol; (c) about 0.1 mM to about 10 mM of at least one buffer; and (d) water; wherein the solution has a pH in the range of 4.0 to 7.5 and does not contain a chelating agent.

Another aspect of the invention provides a method of improving visual performance in a patient. The method comprises administering to the eye of a patient in need thereof an effective amount of an aqueous ophthalmic solution described herein to improve visual performance in the patient. In certain embodiments, the improvement in visual performance is improved visual acuity, such as an improvement in visual acuity under scotopic conditions, mesopic conditions, and/or photopic conditions.

Another aspect of the invention provides a method of reducing pupil diameter in a patient. The method comprises administering to the eye of a patient in need thereof an effective amount of an aqueous ophthalmic solution described herein to reduce pupil diameter in a patient. In certain embodiments, the reduction in pupil diameter under mesopic conditions is at least 5% compared to the pupil diameter of the patient under the same mesopic conditions but not having received said aqueous ophthalmic solution.

Another aspect of the invention provides a method of reducing an aberrant focus of scattered light rays in a patient's eye. The method comprises administering to the eye of a patient in need thereof an effective amount of an aqueous ophthalmic solution described herein to reduce aberrant focus of scattered light rays in the patient's eye.

BRIEF DESCRIPTION OF THE FIGURES

FIG. 3D is a line graph of percent of initial concentration of phentolamine mesylate remaining vs time for solutions stored at 40° C. containing (1) phentolamine mesylate and mannitol (abbreviated P/M); (2) phentolamine mesylate, mannitol and acetate buffer without HPMC (abbreviated P/M/A); (3) phentolamine mesylate, mannitol and acetate buffer with HPMC (abbreviated P/M/A/H); or (4) the Nova Formulation (identified as "Nova" in the figure legend).

DETAILED DESCRIPTION OF THE INVENTION

Figure 1A:
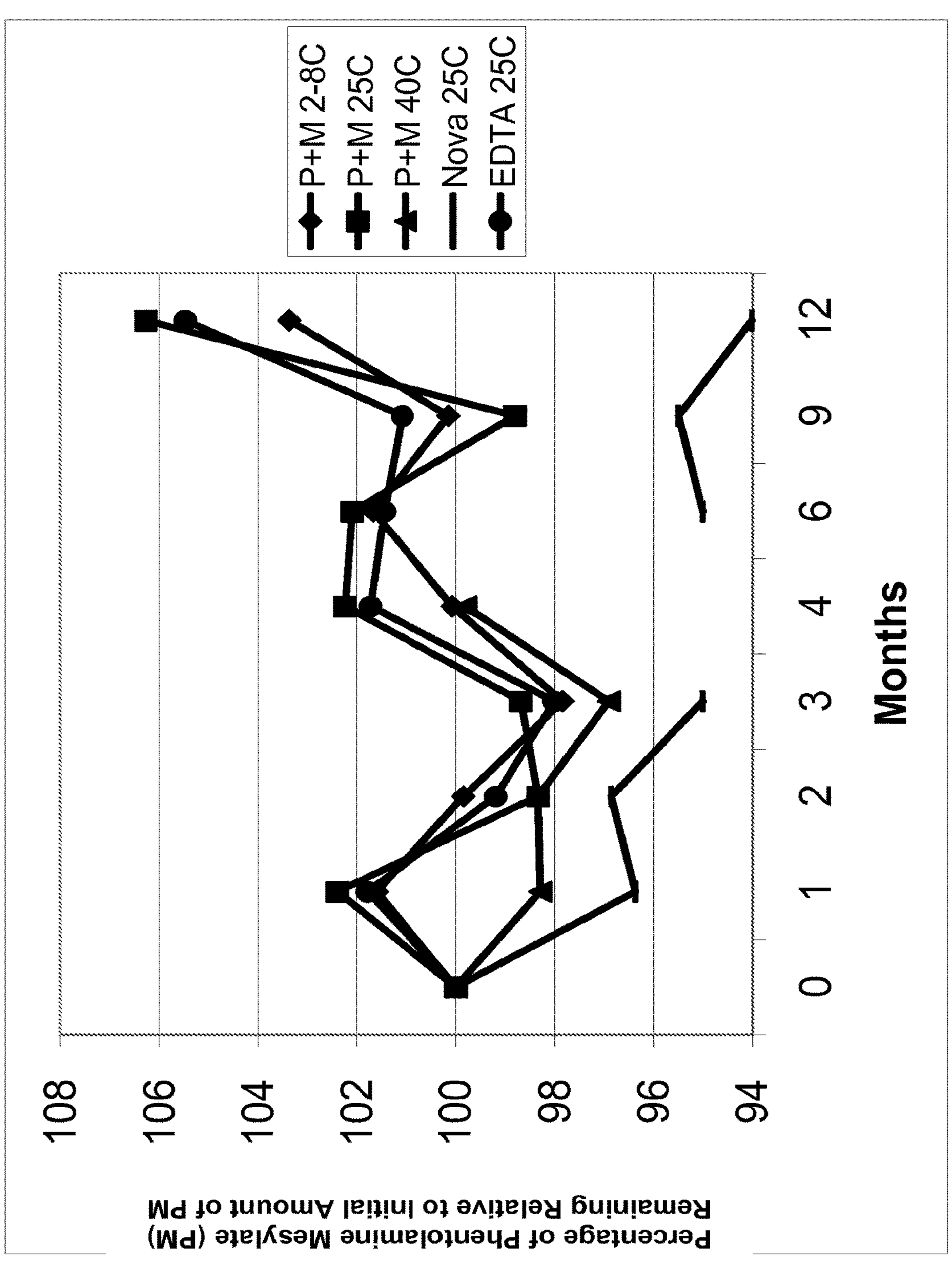
FIG. 1A is a line graph of percent of initial concentration of phentolamine mesylate remaining vs time for solutions stored at, for example, 2-8° C., 25° C., and 40° C.

The invention provides aqueous ophthalmic solutions of phentolamine or pharmaceutically acceptable salts thereof, medical kits, and methods for using such solutions to improve visual performance in a patient. The aqueous ophthalmic solutions have surprisingly been found to be stable to extended storage, even though they do not have a chelating agent. The aqueous ophthalmic solutions described herein offer the additional benefit that they are well-suited for administration to the eye of a patient in the form of an eye drop. For example, the aqueous ophthalmic solutions avoid or minimize any burning or stinging sensation often associated with certain phentolamine mesylate solutions described in the literature. The practice of the present invention employs, unless otherwise indicated, conventional techniques of organic chemistry and pharmacology. Various aspects of the invention are set forth below in sections; however, aspects of the invention described in one particular section are not to be limited to any particular section.

I. Definitions

To facilitate an understanding of the present invention, a number of terms and phrases are defined below.

The terms "a" and "an" as used herein mean "one or more" and include the plural unless the context is inappropriate.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term “Dextran 70” is art-recognized and refers to dextran having a weight average molecular weight of about 70,000 g/mol.

The abbreviation “q.s.” is art-recognized and refers to “quantity sufficient,” meaning the amount of material necessary to bring the solution to the total volume.

The compounds of the disclosure may contain one or more chiral centers and/or double bonds and, therefore, exist as stereoisomers, such as geometric isomers, enantiomers or diastereomers. The term “stereoisomers” when used herein consist of all geometric isomers, enantiomers or diastereomers. These compounds may be designated by the symbols “R” or “S,” depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated “(±)” in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present invention. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the “Z” or “E” configuration wherein the terms “Z” and “E” are used in accordance with IUPAC standards.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances.

As used herein, the terms “subject” and “patient” refer to organisms to be treated by the methods of the present invention. Such organisms are preferably mammals (e.g., murines, simians, equines, bovines, porcines, canines, felines, and the like), and more preferably humans.

As used herein, the term “effective amount” refers to the amount of a compound or aqueous ophthalmic solution sufficient to effect beneficial or desired results. An effective amount can be administered in one or more administrations, applications or dosages and is not intended to be limited to a particular formulation or administration route. As used herein, the term “treating” includes any effect, e.g., lessening, reducing, modulating, ameliorating or eliminating, that results in the improvement of the condition, disease, disorder, and the like, or ameliorating a symptom thereof.

As used herein, the term “pharmaceutical composition” refers to the combination of an active agent with a carrier, inert or active, making the composition especially suitable for diagnostic or therapeutic use in vivo or ex vivo.

As used herein, the term “pharmaceutically acceptable carrier” refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see Martin in Remington’s Pharmaceutical Sciences, 15th Ed., Mack Publ. Co., Easton, PA [1975].

As used herein, the term “pharmaceutically acceptable salt” refers to any pharmaceutically acceptable salt (e.g., acid or base) of a compound of the present invention which, upon administration to a subject, is capable of providing a compound of this invention or an active metabolite or residue thereof. As is known to those of skill in the art, “salts” of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate (i.e., mesylate), 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "about" refers to, for example, 10% of the stated value. For example, about 10 mg of material refers to 9-11 mg of material.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

II. Aqueous Ophthalmic Solutions of Phentolamine and Pharmaceutically Acceptable Salts Thereof One aspect of the invention provides aqueous ophthalmic solutions free of a chelating agent. The aqueous ophthalmic solutions comprise (a) phentolamine or a pharmaceutically acceptable salt thereof, (b) at least one polyol compound, such as a polyol compound having a molecular weight less than 250 g/mol; (c) at least one buffer; and (d) water; wherein the solution does not contain a chelating agent. One of the benefits of the aqueous ophthalmic solutions is they have surprisingly been found to be stable to extended storage, even though they do not have a chelating agent. In addition, another benefit of the aqueous ophthalmic solutions is they avoid or minimize any burning or stinging sensation often associated with certain phentolamine mesylate solutions described in the literature. The amount of ingredients in the aqueous ophthalmic solutions may be selected in order to achieve particular performance properties, such as stability to storage, minimize irritation to the eye of a patient, and enhance penetration of phentolamine into the eye of a patient.

One exemplary preferred solution is an aqueous ophthalmic solution free of a chelating agent comprising: (a) about 0.1% (w/v) to about 4% (w/v) of phentolamine or a pharmaceutically acceptable salt thereof, (b) about 1% (w/v) to about 6% (w/v) of at least one polyol compound having a molecular weight less than 250 g/mol; (c) about 0.1 mM to about 10 mM of at least one buffer; and (d) water; wherein the solution has a pH in the range of 4.0 to 7.5 and does not contain a chelating agent.

Exemplary components and features of the aqueous ophthalmic solution are described in more detail below.

Phentolamine & Pharmaceutically Acceptable Salts

The aqueous ophthalmic solution comprises phentolamine or a pharmaceutically acceptable salt of phentolamine. Exemplary pharmaceutically acceptable salts include, for example, the hydrochloric acid salt and mesylate salt. Accordingly, in certain embodiments, the solution comprises phentolamine (i.e., as the free base). In certain other embodiments, the solution comprises phentolamine hydrochloride. In certain yet other embodiments, the solution comprises phentolamine mesylate.

The amount of phentolamine or a pharmaceutically acceptable salt thereof in the aqueous ophthalmic solution may be adjusted in order to achieve desired performance properties. For example, where is it desired to provide a larger amount of phentolamine (or pharmaceutically acceptable salt thereof) to the patient in a single administration of the aqueous ophthalmic solution, the concentration of phentolamine (or pharmaceutically acceptable salt thereof) is increased in the aqueous ophthalmic solution. Single administration of aqueous ophthalmic solutions having a higher concentration of phentolamine (or pharmaceutically acceptable salt thereof) may provide the patient with improved visual performance for a longer duration of time because more phentolamine (or pharmaceutically acceptable salt thereof) is administered to the patient.

Accordingly, in certain embodiments, the aqueous ophthalmic solution comprises from about 0.1% (w/v) to about 2% (w/v) of phentolamine or a pharmaceutically acceptable salt thereof. In certain embodiments, the aqueous ophthalmic solution comprises from about 0.25% (w/v) to about 2% (w/v) of phentolamine or a pharmaceutically acceptable salt thereof. In certain other embodiments, the aqueous ophthalmic solution comprises from about 0.5% (w/v) to about 2% (w/v) of phentolamine or a pharmaceutically acceptable salt thereof. In certain other embodiments, the aqueous ophthalmic solution comprises from about 0.25% (w/v) to about 1% (w/v) of phentolamine or a pharmaceutically acceptable salt thereof. In certain other embodiments, the aqueous ophthalmic solution comprises about 1% (w/v) of phentolamine or a pharmaceutically acceptable salt thereof. In certain other embodiments, the aqueous ophthalmic solution comprises from about 0.1% (w/v) to about 4% (w/v) of phentolamine mesylate. In certain other embodiments, the aqueous ophthalmic solution comprises from about 0.1% (w/v) to about 2% (w/v) of phentolamine mesylate. In certain other embodiments, the aqueous ophthalmic solution comprises from about 0.25% (w/v) to about 2% (w/v) of phentolamine mesylate. In certain other embodiments, the aqueous ophthalmic solution comprises from about 0.5% (w/v) to about 2% (w/v) of phentolamine mesylate. In certain other embodiments, the aqueous ophthalmic solution comprises from about 0.25% (w/v) to about 1% (w/v) of phentolamine mesylate. In certain other embodiments, the aqueous ophthalmic solution comprises about 1% (w/v) of phentolamine mesylate. In certain other embodiments, the aqueous ophthalmic solution comprises about 0.25% (w/v) or about 0.5% (w/v) of phentolamine mesylate.

Polyol Compounds

The aqueous ophthalmic solution comprises one or more polyol compounds. The polyol compound is an organic compound having at least two hydroxyl groups (e.g., from 2 to about 6 hydroxyl groups). The polyol compound is beneficial to the aqueous ophthalmic solution because, for example, it can increase the stability of the aqueous ophthalmic solution to storage and/or modify the tonicity of the aqueous ophthalmic solution. Exemplary polyol compounds include, for example, mannitol, glycerol, propylene glycol, ethylene glycol, sorbitol, and xylitol.

The aqueous ophthalmic solution may contain a single polyol compound or a mixture of one or more polyol compounds. In other words, the aqueous ophthalmic solution comprises at least one polyol compound. In certain embodiments, the aqueous ophthalmic solution comprises at least one polyol compound that is mannitol, glycerol, propylene glycol, ethylene glycol, sorbitol, or xylitol. In certain other embodiments, the at least one polyol compound is mannitol. In certain other embodiments, the at least one polyol compound is glycerol. In certain other embodiments, the at least one polyol compound is propylene glycol. In certain other embodiments, the at least one polyol compound is mannitol, and the solution further comprises glycerol. In certain other embodiments, the at least one polyol compound is mannitol, and the solution further comprises propylene glycol. In certain other embodiments, the at least one polyol compound is glycerol, and the solution further comprises propylene glycol. In certain other embodiments, the mannitol described in embodiments above is D-mannitol.

The amount of the at least one polyol compound in the aqueous ophthalmic solution may be selected in order to achieve desired performance properties for the solution. The polyol compound may, for example, increase the stability of the solution to storage and/or modify the tonicity of the solution to make it more suitable for administration to the eye of a patient. In certain embodiments, the aqueous ophthalmic solution comprises from about 2% (w/v) to about 5% (w/v) of the at least one polyol compound. In certain other embodiments, the aqueous ophthalmic solution comprises from about 3.5% (w/v) to about 4.5% (w/v) of the at least one polyol compound. In certain other embodiments, the aqueous ophthalmic solution comprises about 4% (w/v) of the at least one polyol compound. In certain other embodiments, the aqueous ophthalmic solution comprises from about 2% (w/v) to about 3% (w/v) mannitol, and about 0.5% (w/v) to about 1.5% (w/v) glycerin. In certain other embodiments, the mannitol described in embodiments above is D-mannitol.

In certain embodiments, the amount of polyol may be selected based on the amount of phentolamine (or pharmaceutically acceptable salt thereof), such that there is an inverse relationship between the amount of phentolamine (or pharmaceutically acceptable salt thereof) and the polyol in order to achieve isotonicity with the eye. For example, in embodiments where the aqueous ophthalmic solution contains about 2% (w/v) phentolamine, mannitol is present in the solution at a concentration of about 3% (w/v). In embodiments where the aqueous ophthalmic solution contains about 1% (w/v) phentolamine, mannitol is present in the solution at a concentration of about 4% (w/v). To further illustrate this principle, in embodiments where the aqueous ophthalmic solution contains about 0.5% (w/v) phentolamine, mannitol may be present in the solution at a concentration of about 4.5% (w/v). In certain embodiments, the mannitol described in embodiments above is D-mannitol.

It is appreciated that the aqueous ophthalmic solution can contain additional ingredients described herein, such as various polymer materials. One such embodiment is an aqueous ophthalmic solution comprising, for example, at least one polyol compound that is propylene glycol, and further comprising polypropylene glycol, such as polypropylene glycol having a weight average molecular weight in the range of about 5,000 g/mol to about 100,000 g/mol.

Poly($C_{2-4}$alkylene)glycol Polymer

The aqueous ophthalmic solution may optionally comprise a poly($C_{2-4}$alkylene)glycol polymer. An exemplary poly($C_{2-4}$alkylene)glycol polymer is polypropylene glycol, such as a polypropylene glycol having a weight average molecular weight in the range of about 5,000 g/mol to about 100,000 g/mol, about 10,000 g/mol to about 50,000 g/mol, or about 50,000 g/mol to about 100,000 g/mol.

Dextran

The aqueous ophthalmic solution may optionally comprise dextran. Dextran is a commercially available, branched polysaccharide comprising glucose molecules. The amount of dextran in the aqueous ophthalmic solution may be selected to achieve certain performance properties. In certain embodiments, the aqueous ophthalmic solution comprises from about 0.01% (w/v) to about 2% (w/v) dextran. In certain other embodiments, the aqueous ophthalmic solution comprises from about 0.01% (w/v) to about 1% (w/v) dextran.

The dextran may be further characterized according to its weight average molecular weight. In certain embodiments, the dextran has a weight average molecular weight in the range of about 65,000 g/mol to about 75,000 g/mol. In certain other embodiments, the dextran has a weight average molecular weight of about 70,000 g/mol. In yet other embodiments, the dextran has a weight average molecular weight in the range of about 5,000 g/mol to about 100,000 g/mol, about 10,000 g/mol to about 50,000 g/mol, or about 50,000 g/mol to about 100,000 g/mol.

Cellulose Agent

The aqueous ophthalmic solution may optionally comprise a cellulose agent. Exemplary cellulose agents include, for example, cellulose, carboxymethyl cellulose, hydroxyethylcellulose, hydroxpropylcellulose, and hydroxypropylmethyl cellulose. In certain embodiments, the cellulose agent is hydroxypropylmethyl cellulose. In certain other embodiments, the cellulose agent is cellulose, carboxymethyl cellulose, hydroxyethylcellulose, or hydroxpropylcellulose. The amount of cellulose agent in the aqueous ophthalmic solution may be selected in order to achieve desired performance properties. For example, in certain embodiments, the aqueous ophthalmic solution comprises from about 0.01% (w/v) to about 2% (w/v) cellulose agent.

The cellulose agent may be further characterized according to its weight average molecular weight. In certain embodiments, the cellulose agent has a weight average molecular weight in the range of about 5,000 g/mol to about 100,000 g/mol, about 10,000 g/mol to about 50,000 g/mol, or about 50,000 g/mol to about 100,000 g/mol.

Buffer

The aqueous ophthalmic solution comprises at least one buffer. The buffer imparts to the solution a buffering capacity, that is, the capacity to neutralize, within limits, either acids or bases (alkali) with relatively little or no change in the original pH. The buffer may be an acid, a base, or a combination of an acid and a base. The buffer may be organic, inorganic, or a combination of organic and inorganic components. It should be understood that the buffer at least partially dissociates in aqueous solution to form a mixture of, e.g., an acid and conjugate base or a base and conjugate acid. For example, the buffer may be a combination of a carboxylic acid and its carboxylate salt. In another embodiment, the buffer may be a combination of an acid and a base, where the acid and the base are not conjugates. For example, the acid may be boric acid and the base may be tris(hydroxymethyl)aminomethane (TRIS).

Exemplary buffers include organic acids (e.g., acetic acid, sorbic acid, and oxalic acid), a borate salt, a hydrogen carbonate salt, a carbonate salt, a gluconate salt, a lactate salt, a phosphate salt, a propionate salt, a perborate salt, tris-(hydroxymethyl)amineomethane (TRIS), bis(2-hydroxyethyl)-imino-tris-(hydroxymethyl)aminoalcohol (bis-tris), N-[2-hydroxy-1,1-bis(hydroxymethyl)ethyl]glycine (tricene), N-[2-hydroxy-1,1-bis(hydroxymethyl)ethyl]glycine, 3-(N-morpholino)propanesulfonic acid, N-(carbamoylmethyl)taurine (ACES), an amino acid, salts thereof, and combinations thereof. It should be understood that the salt form of a buffer may comprise any suitable counterion. For example, the salt form of an acid may comprise an alkali or alkaline earth metal counterion.

The buffer can be characterized according to its strength, i.e., the buffering capacity. The buffering capacity can be tested, for example, by determining the millimoles (mM) of strong acid or base (or respectively, hydrogen or hydroxide ions) required to change the pH of a buffer solution by one unit when added to one liter (a standard unit) of the buffer solution. The buffering capacity generally depends on the type and concentration of the buffer components and can be greater in particular pH ranges. For example, a buffer may have an optimal buffering capacity in a pH range near the $pK_a$ of the buffer, e.g., within about 1 pH unit or within about 2 pH units of the $pK_a$ the buffer. In certain embodiments, the buffer is a weak buffer, such as an alkali metal carboxylate (e.g., sodium acetate).

In certain embodiments, the buffer is a weak acid buffer having one or more of the following characteristics: (a) a pKa of between about 4.0 and about 6.0; more preferably, between about 4.5 and about 5.5; and (b) a lipophilicity value Log P of from about −0.50 to about 1.5; more preferably, from about −0.25 to about 1.35.

The amount of buffer can be adjusted in order to achieve desired performance properties for the aqueous ophthalmic solution. For example, in certain embodiments, the buffer may be present at a concentration of less than about 10 mM, less than about 7 mM, less than about 5 mM, less than about 3 mM, or less than about 2 mM. In some embodiments, the buffer may be present at a concentration of from about 1 mM to about 10 mM, from about 1 mM to about 7 mM, from about 1 mM to about 5 mM, from about 1 mM to about 3 mM, from about 1 mM to about 2 mM, from about 2 mM to about 5 mM, or from about 2 mM to about 3 mM. In yet other embodiments, the buffer is present at a concentration of about 3 mM.

The amount and identity of the buffer may be selected in order to achieve certain performance properties for the aqueous ophthalmic solution. For example, the amount of buffer may impact the quantity of acid that may be neutralized before there is substantial change in the pH of the aqueous ophthalmic solution. Also, the amount of buffer may impact the tonicity of the aqueous ophthalmic solution. Desirably, the quantity and identity of the buffer should be selected in order to minimize any irritation that may be caused by administration of the aqueous ophthalmic solution to the eye of a patient. Accordingly, in certain embodiments, the buffer is present at a concentration in the range of about 2 mM to about 4 mM. In yet other embodiments, the buffer is present at a concentration of about 3 mM. In certain embodiments, the buffer comprises an alkali metal alkylcarboxylate. In certain other embodiments, the buffer comprises an alkali metal acetate. In yet other embodiments, the buffer comprises sodium acetate.

Solution pH

The aqueous ophthalmic solution may be characterized according to the pH of the solution. Desirably, the aqueous ophthalmic solution has a pH in the range of 4.0 to 7.5. In certain embodiments, the aqueous ophthalmic solution has a pH in the range of 4.5 to 7.5. In certain embodiments, the solution has a pH in the range of 4.5 to 6.0. In certain other embodiments, the solution has a pH in the range of 4.5 to 5.5. In yet other embodiments, the solution has a pH in the range of 4.7 to 5.1.

Additional Materials for Aqueous Ophthalmic Solutions

The aqueous ophthalmic solutions may contain additional materials in order to make the composition more suitable for administration to the eye of a patient. Exemplary additional materials are described below and include, for example, a tonicity modifier, preservative, antioxidant, viscosity modifying agent, stabilizing agent, corneal permeation enhancing agent, and surfactants.

A. Tonicity Modifier

The aqueous ophthalmic solution may optionally comprise one or more tonicity modifiers. The tonicity modifier may be ionic or non-ionic. In certain embodiments, the tonicity modifier may be a salt, a carbohydrate, or a polyol. Exemplary tonicity modifiers include alkali metal or alkaline earth metal halides (such as LiBr, LiCl, LiI, KBr, KCl, KI, NaBr, NaCl, NaI, $CaCl_2$), and $MgCl_2$), boric acid, dextran (e.g., Dextran 70), cyclodextrin, dextrose, mannitol, glycerin, urea, sorbitol, propylene glycol, or a combination thereof.

It is appreciated that the tonicity modifier may be added to the aqueous ophthalmic solution in an amount sufficient to provide a desired osmolality. In certain embodiments, the tonicity modifier is present in the aqueous ophthalmic solution in an amount sufficient so that the aqueous ophthalmic solution has an osmolality ranging from about 50 to about 1000 mOsm/kg, from about 100 to about 400 mOsm/kg, from about 200 to about 400 mOsm/kg, or from about 280 to about 380 mOsm/kg. In certain embodiments, a tonicity modifier may be present in an amount ranging from about 0.01% (w/v) to about 7% (w/v), about 0.01% (w/v) to about 5% (w/v), about 0.01% (w/v) to about 1% (w/v), about 0.1% (w/v) to about 1% (w/v), about 0.05% (w/v) to about 50% (w/v), about 0.05% (w/v) to about 0.5% (w/v), about 1% (w/v) to about 3% (w/v), or about 2% (w/v) to about 4% (w/v), of the aqueous ophthalmic solution.

B. Preservative

The aqueous ophthalmic solution may optionally comprise one or more preservatives in order to, for example, reduce or prevent microbial contamination. Exemplary preservatives include quaternary ammonium salts such as polyquaternium-1, cetrimide, benzalkonium chloride, or benzoxonium chloride; alkyl-mercury salts of thiosalicylic acid such as thiomersal, phenylmercuric nitrate, phenylmercuric acetate, or phenylmercuric borate; parabens such as methylparaben or propylparaben; alcohols such as chlorobutanol, benzyl alcohol, phenyl ethanol, cyclohexanol, 3-pentanol, or resorcinol; a peroxide; chlorine dioxide or PURITE; guanidine derivatives such as chlorohexidine gluconate or polyaminopropyl biguanide; and combinations thereof.

The amount of preservative can be adjusted in order to achieve desired performance properties for the aqueous ophthalmic solution. In certain embodiments, the preservative is present in an amount less than about 5% (w/v), 3% (w/v), 1% (w/v), or 0.1% (w/v) of the aqueous ophthalmic solution. In certain other embodiments, the preservative is present in an amount ranging from about 0.01% (w/v) to about 5% (w/v), about 0.01% (w/v) to about 1% (w/v), about 0.1% (w/v) to about 1% (w/v), about 0.05% (w/v) to about 50% (w/v), or about 0.05% (w/v) to about 0.5% (w/v), of the aqueous ophthalmic solution.

C. Antioxidant

The aqueous ophthalmic solution may optionally comprise one or more antioxidants. Exemplary antioxidants for use in the aqueous ophthalmic solutions described herein include water soluble antioxidants such as ascorbic acid, cysteine hydrochloride, sodium bisulfate, sodium metabisulfite, sodium bisulfite, sodium sulfite, and the like; and oil-soluble antioxidants, such as ascorbyl palmitate, butylated hydroxyanisole (BHA), butylated hydroxytoluene (BHT), lecithin, propyl gallate, alpha-tocopherol, and the like.

The amount of antioxidant can be adjusted in order to achieve desired performance properties for the aqueous ophthalmic solution. In certain embodiments, the antioxidant is present in an amount less than about 5% (w/v), 3% (w/v), 1% (w/v), or 0.1% (w/v) of the aqueous ophthalmic solution. In certain other embodiments, the antioxidant is present in an amount ranging from about 0.01% (w/v) to about 5% (w/v), about 0.01% (w/v) to about 1% (w/v), about 0.10% (w/v) to about 10% (w/v), about 0.05% (w/v) to about 50% (w/v), or about 0.05% (w/v) to about 0.5% (w/v), of the aqueous ophthalmic solution.

D. Viscosity Modifying Agent

The aqueous ophthalmic solution may optionally comprise one or more viscosity modifying agents. The viscosity modifying agent may be used, for example, to increase the absorption of an active agent or increase the retention time of the aqueous ophthalmic solution in the eye. Exemplary viscosity modifying agents include polyvinylpyrrolidone, methylcellulose, hydroxypropyl methylcellulose, hydroxyethylcellulose, hydroxpropylcellulose, carboxymethylcellulose (CMC) and salts thereof (e.g., CMC sodium salt), gelatin, cellulose glycolate, sorbitol, niacinamide, an alpha-cyclodextran, polyvinyl alcohol, polyethylene glycol, hyaluronic acid, a polysachcharaide, a monosaccharide, and combinations thereof.

The amount of viscosity modifying agent can be adjusted in order to achieve desired performance properties for the aqueous ophthalmic solution. In certain embodiments, the viscosity modifying agent is present in an amount less than about 10% (w/v), 5% (w/v), 3% (w/v), 1% (w/v), or 0.1% (w/v) of the aqueous ophthalmic solution. In certain other embodiments, the viscosity modifying agent is present in an amount ranging from about 0.01% (w/v) to about 50% (w/v), about 0.010% (w/v) to about 1% (w/v), about 0.10% (w/v) to about 1% (w/v), about 0.05% (w/v) to about 50% (w/v), or about 0.05% (w/v) to about 0.50% (w/v), of the aqueous ophthalmic solution. In certain other embodiments, the viscosity modifying agent is present in an amount sufficient to provide an aqueous ophthalmic solution with a viscosity in the range of about 30 centipoise to about 100 centipoise.

E. Corneal Permeation Enhancing Agent

The aqueous ophthalmic solution may optionally comprise one or more agents for enhancing corneal permeation of phentolamine (or a pharmaceutically acceptable salt thereof). Exemplary agents for enhancing corneal permeation include polymers, organic acids, esters of an organic acid (e.g., a monoglyceride of fatty acid having 8 to 12 carbon atoms), cyclodextrin, benzalkonium chloride (BAK), EDTA, caprylic acid, citric acid, boric acid, sorbic acid, polyoxyethylene-20-stearyl ether (PSE), polyethoxylated castor oil (PCO), deoxycholic acid sodium salt (DC), cetylpyridinium chloride (CPC), laurocapram, hexamethylenelauramide, hexamethyleneoctanamide, decylmethylsulfoxide, methyl sulfone, dimethyl sulfoxide, and combinations thereof.

The amount of corneal permeation enhancing agent can be adjusted in order to achieve desired performance properties for the aqueous ophthalmic solution. In certain embodiments, the corneal permeation enhancing agent is present in an amount less than about 10% (w/v), 5% (w/v), 1% (w/v), or 0.1% (w/v) of the aqueous ophthalmic solution. In certain other embodiments, the corneal permeation enhancing agent is present in an amount ranging from about 0.010% (w/v) to about 50% (w/v), about 0.010% (w/v) to about 10% (w/v), about 0.10% (w/v) to about 10% (w/v), about 0.05% (w/v) to about 50% (w/v), about 0.05% (w/v) to about 0.50% (w/v), about 1% (w/v) to about 3% (w/v), or about 2% (w/v) to about 4% (w/v), of the aqueous ophthalmic solution.

F. Solubilizing Agent

The aqueous ophthalmic solution may optionally comprise one or more solubilizing agents to improve the solubility of phentolamine (or a pharmaceutically acceptable salt thereof) in the aqueous ophthalmic solution. Exemplary solubilizing agents include, for example, a fatty acid glycerol poly-lower alkylene (i.e., a $C_1$ to $C_7$, linear or branched) glycol ester, fatty acid poly-lower alkylene glycol ester, polyalkylene glycol (e.g., polyethylene glycol), glycerol ether of vitamin E, tocopherol polyethylene glycol 1000 succinate (TPGS), tyloxapol, polysorbate 20, polysorbate 40, polysorbate 60, polysorbate 80, polyoxyethylene/polyoxypropylene surfactants (e.g., Pluronic F-68, F-84 and P-103), cyclodextrin, and combinations thereof.

The amount of solubilizing agent can be adjusted in order to achieve desired performance properties for the aqueous ophthalmic solution. In certain embodiments, the solubilizing agent is present in an amount less than about 10% (w/v), 5% (w/v), 3% (w/v), 1% (w/v), or 0.1% (w/v) of the aqueous ophthalmic solution. In certain other embodiments, the solubilizing agent is present in an amount ranging from about 0.01% (w/v) to about 5% (w/v), about 0.010% (w/v) to about 10% (w/v), about 0.10% (w/v) to about 10% (w/v), about 0.0% (w/v) to about 5% (w/v), or about 0.05% (w/v) to about 0.5% (w/v), of the aqueous ophthalmic solution.

G. Stabilizing Agent

The aqueous ophthalmic solution may optionally comprise one or more stabilizing agents in order to improve the stability of the aqueous ophthalmic solution to storage, etc. Stabilizing agents described in the pharmaceutical literature are contemplated to be amenable for use in the aqueous ophthalmic solutions described herein. Exemplary stabilizing agents include an alcohol (e.g., polyols, such as mannitol, glycerol, propylene glycol, sorbitol, and xylitol), polyalkylene glycols such as polyethylene glycol, polypropylene glycol, polyethylene glycol-nonphenol ether, polyethylene glycol sorbitan monolaurate, polyethylene glycol sorbitan monooleate, polyethylene glycol sorbitan monooleate, polyethylene glycol sterarate, polyethylene glycol polypropylene glycol ether, polyvinyl alcohol, polyvinyl pyrrolidine, ascorbic acid, vitamin E, N-acetylcarnosine (NAC), sorbic acid, and combinations thereof. In certain embodiments, the stabilizing agent is a polymer, such as one of the polymers mentioned above.

The amount of stabilizing agent can be adjusted in order to achieve desired performance properties for the aqueous ophthalmic solution. In certain embodiments, the stabilizing agent is present in an amount less than about 10% (w/v), 5% (w/v), or 1% (w/v) of the aqueous ophthalmic solution. In certain other embodiments, the stabilizing agent is present in an amount ranging from about 0.01% (w/v) to about 5% (w/v), about 0.01% (w/v) to about 1% (w/v), or about 0.01% (w/v) to about 0.1% (w/v) of the aqueous ophthalmic solution.

H. Surfactant

The aqueous ophthalmic solution may optionally comprise one or more surfactants. Exemplary surfactants include Polysorbate 20 (i.e., polyoxyethylene (20) sorbitan monolaurate), Polysorbate 40 (i.e., polyoxyethylene (20) sorbitan monopalmitate), Polysorbate 60 (i.e., polyoxyethylene (20) sorbitan monostearate), Polysorbate 80 (i.e., polyoxyethylene (20) sorbitan monooleate), glyceryl stearate, isopropyl stearate, polyoxyl stearate, propylene glycol stearate, sucrose stearate, polyethylene glycol, a polypropylene oxide, a polypropylene oxide copolymer, Pluronic F68, Pluronic F-84, Pluronic P-103, an alcohol ethoxylate, an alkylphenol ethoxylate, an alkyl glycoside, an alkyl polyglycoside, a fatty alcohol, hydroxypropylmethyl cellulose (HPMC), carboxymethyl cellulose (CMC), cyclodextrin, a polyacrylic acid, phosphatidyl chloline, phosphatidyl serine, and combinations thereof.

The amount of surfactant can be adjusted in order to achieve desired performance properties for the aqueous ophthalmic solution. In certain embodiments, the surfactant is present in an amount less than about 10% (w/v), 5% (w/v), 3% (w/v), 1% (w/v), or 0.1% (w/v) of the aqueous ophthalmic solution. In certain other embodiments, the surfactant is present in an amount ranging from about 0.01% (w/v) to about 5% (w/v), about 0.01% (w/v) to about 1% (w/v), about 0.10% (w/v) to about 10% (w/v), about 0.05% (w/v) to about 50% (w/v), or about 0.05% (w/v) to about 0.5% (w/v), of the aqueous ophthalmic solution.

I. Demulcent Polymers

The aqueous ophthalmic solution may optionally comprise one or more demulcent polymers. Because of their ability to hold large amounts of water, demulcent polymers are useful for coating and moisturizing the cornea of the eye. Exemplary demulcent polymers include cellulose derivatives, dextran 40, dextran 70, gelatin, and liquid polyols.

J. Wetting Agents

The aqueous ophthalmic solution may optionally comprise one or more wetting agents. Wetting agents can be used to wet the surface of the eye. Exemplary wetting agents include polysorbates, poloxamers, tyloxapol, and lecithin.

K. Additional Materials

The aqueous ophthalmic solutions may optionally comprise one or more additional materials, such as acetylcysteine, cysteine, sodium hydrogen sulfite, butyl-hydroxyanisole, butyl-hydroxytoluene, alpha-tocopherol acetate, thiourea, thiosorbitol, sodium dioctyl sulfosuccinate, monothioglycerol, lauric acid sorbitol ester, triethanol amine oleate, or palmitic acid esters.

Further, the aqueous ophthalmic solutions may comprise a carrier, such as one or more of the exemplary carriers are described in for example, Martin, Remington's Pharmaceutical Sciences, 15th Ed., Mack Publ. Co., Easton, PA [1975]). The carrier can be, for example, a mixture of water and a water-miscible solvent (e.g., an alcohol such as glycerin, a vegetable oil, or a mineral oil). Other exemplary carriers include a mixture of water and one or more of the following materials: hydroxyethylcellulose, carboxymethylcellulose, methylcellulose, an alkali metal salt of carboxymethylcellulose, hydroxymethylcellulose, methylhydroxypropylcellulose, hydroxypropylcellulose, ethyl oleate, polyvinylpyrrolidone, an acrylate polymer, a methacrylate polymer, a polyacrylamide, gelatin, an alginate, a pectin, tragacanth, karaya gum, xanthan gum, carrageenin, agar, acacia, a starch (such as starch acetate or hydroxypropyl starch), polyvinyl alcohol, polyvinyl methyl ether, polyethylene oxide, or a cross-linked polyacrylic acid.

Exemplary Aqueous Ophthalmic Solutions

The aqueous ophthalmic solutions having been generally described above will now be more specifically described by reference to the following more specific examples. The following more specific examples are only exemplary and are not intended to limit the scope of the invention in any way.

One such exemplary solution is an aqueous ophthalmic solution free of a chelating agent comprising: (a) about 0.1% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4 to 6 and does not contain a chelating agent.

The aqueous ophthalmic solution may be more specifically defined according to the following embodiments. For example, in certain embodiments, the aqueous ophthalmic solution comprises from about 0.25% (w/v) to about 1% (w/v) of phentolamine mesylate. In certain embodiments, the aqueous ophthalmic solution comprises from about 1% (w/v) to about 4% (w/v) mannitol. In certain other embodiments, the aqueous ophthalmic solution comprises 4% (w/v) mannitol. In certain embodiments, the alkali metal acetate is sodium acetate. In certain other embodiments, the aqueous ophthalmic solution comprises 3 mM sodium acetate. In still other embodiments, the aqueous ophthalmic solution consists of (i) about 0.25% (w/v) to about 1% (w/v) of phentolamine mesylate; (ii) about 1% (w/v) to about 6% (w/v) of one or more polyol compounds selected from the group consisting of mannitol, glycerol, and propylene glycol; (iii) about 1 mM to about 6 mM of an alkali metal acetate; (iv) acetic acid; and (v) water; wherein the solution has a pH in the range of 4 to 6.

Another such exemplary solution is an aqueous ophthalmic solution free of a chelating agent comprising: (a) about 0.5% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4.5 to 5.5 and does not contain a chelating agent.

The aqueous ophthalmic solution may be more specifically defined according to the following embodiments. For example, in certain embodiments, the aqueous ophthalmic solution comprises from about 1% (w/v) to about 4% (w/v) mannitol. In certain other embodiments, the aqueous ophthalmic solution comprises 4% (w/v) mannitol. In certain embodiments, the alkali metal acetate is sodium acetate. In certain other embodiments, the aqueous ophthalmic solution comprises 3 mM sodium acetate. In still other embodiments, the aqueous ophthalmic solution consists of (i) about 0.5% (w/v) to about 2% (w/v) of phentolamine mesylate; (ii) about 1% (w/v) to about 6% (w/v) of one or more polyol compounds selected from the group consisting of mannitol, glycerol, and propylene glycol; (iii) about 1 mM to about 6 mM of an alkali metal acetate; (iv) acetic acid; and (v) water; wherein the solution has a pH in the range of 4.5 to 5.5.

Another such exemplary solution is an aqueous ophthalmic solution free of a chelating agent comprising: (a) about 0.25% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4.5 to 5.5 and does not contain a chelating agent.

The aqueous ophthalmic solution may be more specifically defined according to the following embodiments. For example, in certain embodiments, the aqueous ophthalmic solution comprises from about 0.25% (w/v) to about 1% (w/v) of phentolamine mesylate. In certain other embodiments, the aqueous ophthalmic solution comprises from about 10 (w/v) to about 40 (w/v) mannitol. In certain other embodiments, the aqueous ophthalmic solution comprises 40% (w/v) mannitol. In certain embodiments, the alkali metal acetate is sodium acetate. In certain other embodiments, the aqueous ophthalmic solution comprises 3 mM sodium acetate. In still other embodiments, the aqueous ophthalmic solution consists of (i) about 0.5% (w/v) to about P % (w/v) of phentolamine mesylate; (ii) about. (w/v) to about 6% (w/v) of one or more polyol compounds selected from the group consisting of mannitol, glycerol, and propylene glycol; (iii) about 1 mM to about 6 mM of an alkali metal acetate; (iv) acetic acid; and (v) water; wherein the solution has a pH in the range of 4.5 to 5.5.

Further exemplary aqueous ophthalmic solutions are provided in Tables 1-3 below, where in each instance the solution has a pH in the range of 4.7 to 5.1.

TABLE 1

EXEMPLARY AQUEOUS OPHTHALMIC SOLUTIONS.

| | Formulation No. | | | | | | | |
|---|---|---|---|---|---|---|---|---|
| Component | A1 | B1 | C1 | D1 | E1 | F1 | G1 | H1 |
| Phentolamine mesylate (% w/v) | 1.5 | 1 | 0.5 | 1 | 1 | 1 | 1 | 1 |
| Mannitol (% w/v) | 4 | 4 | 4 | 3 | 3 | 2 | 2 | 4 |
| Sodium acetate (mM) | 3 | 3 | 3 | 3 | 3 | 3 | 3 | 3 |
| Glycerol (% w/v) | 0 | 0 | 0 | 0.5 | 0 | 1 | 0 | 0 |
| Propylene glycol (% w/v) | 0 | 0 | 0 | 0 | 0.5 | 0 | 1 | 0 |
| Dextran 70 (% w/v) | 0 | 0 | 0 | 0 | 0 | 0 | 0 | 0.1 |
| Water | q.s. | q.s. | q.s. | q.s. | q.s. | q.s. | q.s. | q.s. |

TABLE 2

EXEMPLARY AQUEOUS OPHTHALMIC SOLUTIONS.

| | Formulation No. | | | | | |
|---|---|---|---|---|---|---|
| Component | A2 | B2 | C2 | D2 | E2 | F2 |
| Phentolamine mesylate (% w/v) | 0.25 | 0.25 | 0.25 | 0.25 | 0.25 | 0.25 |
| Mannitol (% w/v) | 4 | 3 | 3 | 2 | 2 | 4 |
| Sodium acetate (mM) | 3 | 3 | 3 | 3 | 3 | 3 |
| Glycerol (% w/v) | 0 | 0.5 | 0 | 1 | 0 | 0 |
| Propylene glycol (% w/v) | 0 | 0 | 0.5 | 0 | 1 | 0 |
| Dextran 70 (% w/v) | 0 | 0 | 0 | 0 | 0 | 0.1 |
| Water | q.s. | q.s. | q.s. | q.s. | q.s. | q.s. |

TABLE 3

EXEMPLARY AQUEOUS OPHTHALMIC SOLUTIONS.

| | Formulation No. | | | | | | | |
|---|---|---|---|---|---|---|---|---|
| Component | A3 | B3 | C3 | D3 | E3 | F3 | G3 | H3 |
| Phentolamine mesylate (% w/v) | 1.5 | 1 | 0.5 | 0.25 | 1 | 1 | 1 | 1 |
| Mannitol (% w/v) | 4 | 4 | 4 | 4 | 3 | 2 | 2 | 4 |
| Sodium acetate (mM) | 3 | 3 | 3 | 3 | 3 | 3 | 2 | 3 |
| Water | q.s. | q.s. | q.s. | q.s. | q.s. | q.s. | q.s. | q.s. |

Another exemplary aqueous ophthalmic solution comprises phentolamine mesylate (e.g., at 100 w/v), mannitol (e.g., at 400 w/v), dextran having a weight average molecular weight of about 70,000 g/mol (e.g., at 0.10% w/v), hydroxypropyl methylcellulose (e.g., at 0.3% w/v), potassium chloride, purified water, sodium borate, and sodium chloride; wherein the solution has a pH in the range of about 4 to about 6. In certain embodiments, the solution has a pH in the range of 4.5 to 5.1. In certain embodiments, the aqueous ophthalmic solution consists essentially of phentolamine mesylate (e.g., at 10% w/v), mannitol (e.g., at 4% w/v), dextran having a weight average molecular weight of about 70,000 g/mol (e.g., at 0.10% w/v), hydroxypropyl methylcellulose (e.g., at 0.30% w/v), potassium chloride, purified water, sodium borate, and sodium chloride; wherein the solution has a pH in the range of 4 to 6. In certain other embodiments, the aqueous ophthalmic solution consists of phentolamine mesylate (e.g., at 10% w/v), mannitol (e.g., at 400 w/v), dextran having a weight average molecular weight of about 70,000 g/mol (e.g., at 0.1% w/v), hydroxypropyl methylcellulose (e.g., at 0.3% w/v), potassium chloride, purified water, sodium borate, and sodium chloride; wherein the solution has a pH in the range of 4.5 to 5.1.

Another exemplary aqueous ophthalmic solution comprises phentolamine mesylate (e.g., at 1% w/v), mannitol (e.g., at 4% w/v), sodium acetate (e.g., at 3 mM), and water, wherein the solution has a pH in the range of about 4 to about 6. In certain embodiments, the solution has a pH in the range of 4.5 to 5.1. In certain embodiments, the aqueous ophthalmic solution consists essentially of phentolamine mesylate (e.g., at 1% w/v), mannitol (e.g., at 4% w/v), sodium acetate (e.g., at 3 mM), and water, wherein the solution has a pH in the range of 4 to 6. In certain embodiments, the aqueous ophthalmic solution comprises phentolamine mesylate at 1% w/v, mannitol 4% w/v, sodium acetate at 3 mM, and water, wherein the solution has a pH in the range of 4.5 to 5.1. In certain other embodiments, the aqueous ophthalmic solution consists of phentolamine mesylate (e.g., at 1% w/v), mannitol (e.g., at 4% w/v), sodium acetate (e.g., at 3 mM), and water, wherein the solution has a pH in the range of 4.5 to 5.1. In certain embodiments, the aqueous ophthalmic solution consists essentially of phentolamine mesylate at 1% w/v, mannitol 4% w/v, sodium acetate at 3 mM, and water, wherein the solution has a pH in the range of 4.5 to 5.1.

Yet another exemplary solution is an aqueous ophthalmic solution free of a chelating agent that comprises: (a) about 0.1% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4 to 6 and does not contain a chelating agent.

Yet another exemplary solution is an aqueous ophthalmic solution free of a chelating agent that comprises: (a) about 0.25% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.6 to 5.2 and does not contain a chelating agent.

Yet another exemplary solution is an aqueous ophthalmic solution free of a chelating agent that comprises: (a) about 0.1% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.6 to 5.2 and does not contain a chelating agent. In certain embodiments, the aqueous ophthalmic solution free of a chelating agent that comprises about 0.25% (w/v) to about 1% (w/v) of phentolamine mesylate.

Yet another exemplary solution is an aqueous ophthalmic solution free of a chelating agent, comprising: (a) about 0.25% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.5 to 5.2 and does not contain a chelating agent.

Yet another exemplary solution is an aqueous ophthalmic solution free of a chelating agent that comprises: (a) about 0.5% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.6 to 5.2 and does not contain a chelating agent.

Yet another exemplary solution is an aqueous ophthalmic solution free of a chelating agent that comprises: (a) about 0.5% (w/v) to about 1% (w/v) of phentolamine mesylate; (b) about 3% (w/v) to about 5% (w/v) of mannitol; (c) about 1 mM to about 4 mM of sodium acetate; and (d) water; wherein the solution has a pH in the range of 4.6 to 5.2 and does not contain a chelating agent.

Yet another exemplary solution is an aqueous ophthalmic solution free of a chelating agent, comprising: (a) about 0.1% (w/v) to about 1% (w/v) of phentolamine mesylate; (b) about 4% mannitol; (c) about 3 mM sodium acetate; and (d) water; wherein the solution has a pH in the range of 4.6 to 5.2 and does not contain a chelating agent. In certain embodiments, the aqueous ophthalmic solution free of a chelating agent that comprises about 0.25% (w/v) to about 1% (w/v) of phentolamine mesylate.

Yet another exemplary solution is an aqueous ophthalmic solution free of a chelating agent, comprising: (a) about 0.5% (w/v) to about 1% (w/v) of phentolamine mesylate; (b) about 4% mannitol; (c) about 3 mM sodium acetate; and (d) water; wherein the solution has a pH in the range of 4.6 to 5.2 and does not contain a chelating agent.

Stability Features of Aqueous Ophthalmic Solutions

The aqueous ophthalmic solutions described herein may be further characterized according to their stability features, such as the percentage of phentolamine (or pharmaceutically acceptable salt thereof) that is present in the aqueous ophthalmic solution after storage for a certain length of time. As explained above, one of the benefits of the present aqueous ophthalmic solutions is that they possess good stability over extended periods of time, even though they do not have a chelating agent.

Accordingly, in certain embodiments, the aqueous ophthalmic solution is characterized by less than 2% of the phentolamine or pharmaceutically acceptable salt thereof degrades upon storage of the solution at 25° C. for 12 weeks. In certain other embodiments, the aqueous ophthalmic solution is characterized by less than 2% of the phentolamine or pharmaceutically acceptable salt thereof degrades upon storage at 25° C. for 24 weeks (or 36 weeks or 48 weeks). In certain other embodiments, the aqueous ophthalmic solution is characterized by less than 10% of the phentolamine or pharmaceutically acceptable salt thereof degrades upon storage at 25° C. for 1 year or 2 years. In yet other embodiments, less than 7% of the phentolamine or pharmaceutically acceptable salt thereof degrades upon storage at 40° C. for 12 weeks (or 24, 36, or 48 weeks). In yet other embodiments, the aqueous ophthalmic solution is characterized by less than 10% by weight of the phentolamine or pharmaceutically acceptable salt thereof degrades upon storage at 25° C. for 18 months, 24 months, or 36 months. In yet other embodiments, the aqueous ophthalmic solution is characterized by less than 10% by weight of the phentolamine or pharmaceutically acceptable salt thereof degrades upon storage at temperature in the range of 2-8° C. for 18 months, 24 months, or 36 months. In yet other embodiments, the aqueous ophthalmic solution is characterized by less than 4% by weight (or preferably less than 3% by weight) of the phentolamine or pharmaceutically acceptable salt thereof degrades upon storage at 25° C. for 18 months, 24 months, or 36 months. In yet other embodiments, less than 10% by weight of the phentolamine or pharmaceutically acceptable salt thereof degrades upon storage at 40° C. for 4, 5, or 6 months.

III. Therapeutic Applications

The invention provides methods of improving vision in a patient using the aqueous ophthalmic solutions described herein.

Methods of Improving Visual Performance

One aspect of the invention provides a method of improving visual performance in a patient. The method comprises administering to the eye of a patient in need thereof an effective amount of an aqueous ophthalmic solutions described herein, such as an aqueous ophthalmic solution described in Section II, to improve visual performance in the patient.

Visual performance pertains to the patient's overall vision quality and includes a patient's ability to see clearly, as well as ability to distinguish between an object and its background. One aspect of visual performance is visual acuity. Visual acuity is a measure of a patient's ability to see clearly. Visual acuity can be measured using, for example, a Snellen chart, and the visual acuity measurement can be taken under conditions that test low-contrast visual acuity or under conditions that test high-contrast visual acuity. Further, the visual acuity measurement can be taken under scotopic conditions, mesopic conditions, and/or photopic conditions. Another aspect of visual performance is contrast sensitivity.

Contrast sensitivity is a measure of the patient's ability to distinguish between an object and its background. Contrast sensitivity can be measured using, for example, a Holladay Automated Contrast Sensitivity System. The contrast sensitivity can be measured under various light conditions, including, for example, photopic conditions, mesopic conditions, and scotopic conditions, each either with or without glare. In certain embodiments, the contrast sensitivity is measured under mesopic conditions either with or without glare.

In certain embodiments, the improvement in visual performance provided by the method is improved visual acuity. In certain embodiments, the improvement in visual performance provided by the method is improved visual acuity under scotopic conditions. In certain embodiments, the improvement in visual performance provided by the method is improved visual acuity under mesopic conditions. In certain embodiments, the improvement in visual performance provided by the method is improved visual acuity under photopic conditions. In certain embodiments, the improvement in visual acuity is a two-line improvement in the patient's vision as measured using the Snellen chart. In certain other embodiments, the improvement in visual acuity is a one-line improvement in the patient's vision as measured using the Snellen chart.

In certain embodiments, the improvement in visual performance provided by the method is improved contrast sensitivity. The improvement in contrast sensitivity can be measured under various light conditions, such as photopic conditions, mesopic conditions, and scotopic conditions. In certain embodiments, the improvement in visual performance provided by the method is improved contrast sensitivity under photopic conditions. In certain embodiments, the improvement in visual performance provided by the method is improved contrast sensitivity under mesopic conditions. In certain embodiments, the improvement in visual performance provided by the method is improved contrast sensitivity under scotopic conditions. Further, contrast sensitivity can be measured in the presence of glare or the absence of glare. All combinations of light conditions and glare are contemplated.

Results achieved by the therapeutic methods can be characterized according to the patient's improvement in contrast sensitivity. For example, in certain embodiments, the improvement in contrast sensitivity is a 10% (or 20%, 30%, 50%, 60%, or 70%) improvement measured under mesopic conditions using the Holladay Automated Contrast Sensitivity System. In certain embodiments, the improvement in contrast sensitivity is a 10% (or 20%, 30%, 50%, 60%, or 70%) improvement measured under photopic conditions using the Holladay Automated Contrast Sensitivity System. In certain other embodiments, the improvement in contrast sensitivity is at least a 10% (or 20%, 30%, 50%, 60%, or 70%) improvement measured under mesopic conditions or scotopic conditions using the Holladay Automated Contrast Sensitivity System.

In certain other embodiments, the improvement in visual performance provided by the method is both (i) improved visual acuity (such as under scotopic conditions, mesopic conditions, and/or photopic conditions) and (ii) improved contrast sensitivity (such as under scotopic conditions, mesopic conditions, and/or photopic conditions).

Methods of Reducing Pupil Diameter

One aspect of the invention provides a method of reducing pupil diameter in a patient. The method comprises administering to the eye of a patient in need thereof an effective amount of an aqueous ophthalmic solution described herein, such as an aqueous ophthalmic solution described in Section II, to reduce pupil diameter in a patient.

The reduction in pupil diameter can be characterized according to, for example, the percent reduction in pupil diameter and size of the pupil measured under certain light conditions. Accordingly, in certain embodiments, the reduction in pupil diameter under mesopic conditions is at least 5% compared to the pupil diameter of the patient under the same mesopic conditions but not having received the aqueous ophthalmic solution. In certain other embodiments, the reduction in pupil diameter under mesopic conditions is at least 10% compared to the pupil diameter of the patient under the same mesopic conditions but not having received the aqueous ophthalmic solution. In certain other embodiments, the patient experiences a reduction in pupil diameter of at least 0.5 mm when measured under mesopic conditions relative to the diameter of the patient's pupil under the same mesopic conditions but not having received the aqueous ophthalmic solution. In certain other embodiments, the patient experiences a reduction in pupil diameter ranging from about 0.6 mm to about 3 mm, about 0.6 mm to about 2.5 mm, or about 0.6 mm to about 2 mm when measured under mesopic conditions relative to the diameter of the patient's pupil under the same mesopic conditions but not having received the aqueous ophthalmic solution. In certain other embodiments, the patient experiences a reduction in pupil diameter ranging from about 0.6 mm to about 1.2 mm when measured under mesopic conditions relative to the diameter of the patient's pupil under the same mesopic conditions but not having received the aqueous ophthalmic solution. In yet other embodiments, the patient's pupil is reduced to a diameter of about 3 mm to about 5 mm, about 3 mm to about 6 mm, about 4 mm to about 5 mm, about 4 mm to about 6 mm, or about 4 mm to about 7 mm under mesopic conditions due to the aqueous ophthalmic solution. In certain embodiments, the patient's pupil is reduced to a diameter of about 4 mm to about 6 mm under mesopic conditions due to the aqueous ophthalmic solution.

In certain other embodiments, the reduction in pupil diameter under scotopic conditions is at least 5% compared to the pupil diameter of the patient under the same scotopic conditions but not having received the aqueous ophthalmic solution. In certain other embodiments, the reduction in pupil diameter under scotopic conditions is at least 10% compared to the pupil diameter of the patient under the same scotopic conditions but not having received the aqueous ophthalmic solution. In certain other embodiments, the patient experiences a reduction in pupil diameter of at least 0.5 mm when measured under scotopic conditions relative to the diameter of the patient's pupil under the same scotopic conditions but not having received the aqueous ophthalmic solution. In certain other embodiments, the patient experiences a reduction in pupil diameter ranging from about 0.6 mm to about 3 mm, about 0.6 mm to about 2.5 mm, or about 0.6 mm to about 2 mm when measured under scotopic conditions relative to the diameter of the patient's pupil under the same scotopic conditions but not having received the aqueous ophthalmic solution. In certain other embodiments, the patient experiences a reduction in pupil diameter ranging from about 0.6 mm to about 1.2 mm when measured under scotopic conditions relative to the diameter of the patient's pupil under the same scotopic conditions but not having received the aqueous ophthalmic solution. In yet other embodiments, the patient's pupil is reduced to a diameter of about 3 mm to about 5 mm, about 3 mm to about 6 mm, about 4 mm to about 5 mm, about 4 mm to about 6 mm, or about 4 mm to about 7 mm under scotopic conditions due to the aqueous ophthalmic solution. In certain embodiments, the patient's pupil is reduced to a diameter of about 4 mm to about 6 mm under scotopic conditions due to the aqueous ophthalmic solution.

Methods of Reducing Aberrant Focus of Scattered Light Rays

One aspect of the invention provides a method of reducing an aberrant focus of scattered light rays in a patient's eye. The method comprises administering to the eye of a patient in need thereof an effective amount of an aqueous ophthalmic solution, such as an aqueous ophthalmic solution described in Section II, to reduce aberrant focus of scattered light rays in the patient's eye.

General Considerations for Therapeutic Methods

The aqueous ophthalmic solution can be administered according to a dosing regimen. For example, in certain embodiments, the aqueous ophthalmic solution is administered at the bedtime of the patient.

The therapeutic method can be further characterized according to the incidence and severity of any adverse side effects associated with administration of the aqueous ophthalmic solution to the patient. Desirably the aqueous ophthalmic solution provides a therapeutic benefit (e.g., improvement in visual performance) while minimizing the impact and/or occurrence of any adverse side effects, such as eye redness sometimes associated with administration of the aqueous ophthalmic solution to the eye of a patient. The degree of eye redness can be evaluated and characterized using procedures described in the literature, such as the Cornea and Contact Lens Research Unit (CCLRU) Redness Grading Scale developed by the School of Optometry, University of New South Wales. See, for example, Terry et al. in *Optom. Vis. Sci.* (1993) vol. 70, pages 234-243; and Pult et al. in *Ophthal. Physiol. Opt.* (2008) vol. 28, pages 13-20. The CCLRU Redness Grading Scale evaluates eye redness on a four-point scale: (0) no eye redness, (1) very slight eye redness, (2) slight eye redness, (3) moderate eye redness, and (4) severe eye redness.

In certain embodiments, the method results in an increase in eye redness of no more than two grades measured by the CCLRU Redness Grading Scale. In certain embodiments, the method results in an increase in eye redness of no more than three grades measured by the CCLRU Redness Grading Scale. In certain embodiments, the method results in an increase in eye redness of no more than one grade when measured using the CCLRU Redness Grading Scale eight hours after administration of the aqueous ophthalmic solution. In certain embodiments, the method results in an increase in eye redness of no more than one grade when measured using the CCLRU Redness Grading Scale six hours after administration of the aqueous ophthalmic solution. In certain embodiments, the method results in an increase in eye redness of no more than two grades when measured using CCLRU Redness Grading Scale two hours after administration of the aqueous ophthalmic solution. In certain other embodiments, any eye redness in the patient due to administration of the aqueous ophthalmic solution has subsided within eight hours after administration of the aqueous ophthalmic solution to the patient. In certain other embodiments, any eye redness in the patient due to administration of the aqueous ophthalmic solution has subsided within six hours after administration of the aqueous ophthalmic solution to the patient.

The therapeutic method can also be characterized according to the magnitude of the improvement in visual acuity afforded by the aqueous ophthalmic solution. For example, in certain embodiments, the method results in an improvement in visual acuity characterized by at least a two-line improvement in the patient's vision measured using a Snellen chart.

In certain embodiments, the patient is a human.

In certain embodiments, the aqueous ophthalmic solution is one of the generic or specific aqueous ophthalmic solutions described in Section II.

The description above describes multiple embodiments relating to therapeutic methods using aqueous ophthalmic solution. The patent application specifically contemplates all combinations of the embodiments. For example, the invention contemplates improving visual acuity under scotopic conditions using an aqueous ophthalmic solution comprising phentolamine mesylate.

Additional Considerations

Actual dosage levels of the active ingredients in the aqueous ophthalmic solution of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the aqueous ophthalmic solution of the present invention employed or salt thereof, the route of administration, the time of administration, the rate of excretion or metabolism of the particular compound being employed, the rate and extent of absorption, the duration of the treatment, other drugs, compounds and/or materials used in combination with the aqueous ophthalmic solution employed, the age, sex, weight, condition, general health and prior medical history of the patient being treated, and like factors well known in the medical arts.

A physician or veterinarian having ordinary skill in the art can readily determine and prescribe the effective amount of the aqueous ophthalmic solution required. For example, the physician or veterinarian could start doses of the aqueous ophthalmic solution at levels lower than that required in order to achieve the desired therapeutic effect and gradually increase the dosage until the desired effect is achieved.

If desired, the effective daily dose of the aqueous ophthalmic solution may be administered as one or two subdoses administered separately at appropriate intervals throughout the day (or week), optionally, in unit dosage forms.

IV. Kits for Use in Medical Applications

Another aspect of the invention provides a kit for medical therapy The kit comprises: i) instructions for improving vision in a patient, such as improving visual performance); and ii) an aqueous ophthalmic solution described herein. The kit may comprise one or more unit dosage forms containing an amount of the aqueous ophthalmic solution described herein effective for improving vision in the patient.

The description above describes multiple aspects and embodiments of the invention, including aqueous ophthalmic solutions, methods of using the aqueous ophthalmic solutions, and kits. The patent application specifically contemplates all combinations and permutations of the aspects and embodiments.

EXAMPLES

The invention now being generally described, will be more readily understood by reference to the following example, which is included merely for purposes of illustration of certain aspects and embodiments of the present invention, and is not intended to limit the invention.

Example 1—Stability Analysis of Aqueous Solution Containing 1% (W/V) Phentolamine Mesylate The purpose of this experiment was to evaluate the stability of aqueous solutions containing phentolamine mesylate over a range of temperatures.

Experimental Design

Phentolamine mesylate (1.0% w/v) was obtained from Spectrum Pharmaceuticals. The HPLC analytical method for analysis of the formulations was developed by Newport Scientific, Inc.

The assay for API, impurities and degradants was performed using Atlantis HILIC 4.6 mm×250 mm×5 m column. The injection volume was 10 μL. Mobile phase A: 10 mM $HCOONH_4$ in water (12%). $HCOONH_4$ (10 mmol, 630 mg) was dissolved in 950 mL water. The pH was adjusted to 3.0 by addition of formic acid. The volume was then completed to 1 L by adding water (50 mL). Mobile phase B: Acetonitrile (88%). The temperature was 35° C., the flow rate was 1 mL/min, the injection volume was 10 μL, and the sample/standard concentration was 100 μg/mL.

Each sample was well shaken and then 0.5 to 1.0 mL were transferred into a clear test tube and physical appearance recorded.

Bottles containing 5.0 mL of 1.0% w/v phentolamine mesylate ophthalmic solution were stored at 2-8° C., 25° C., 40° C., and 60° C. For each tested time point, two bottles were used. Before testing, all samples were allowed to equilibrate to room temperature. Immediately prior to conducting each test, each sample was vigorously shaken. Then, assay for API, impurities and degradants was performed according to the method described above and the physical appearance of the sample was determined. Also, the pH of the sample was determined and measured in duplicate to ensure that there is no drift.

A final report was generated upon completion of the protocol.

Phentolamine mesylate (1.0% w/v) was tested for stability in water over the course of four weeks at the following temperatures: 2-8° C., 25° C., 40° C., and 60° C.

Results

The results of this experiment are provided in Tables 1A-1D. The abbreviation "N/A" indicates that no data are available.

TABLE 1A

AQUEOUS SOLUTION OF 1% (w/v) PHENTOLAMINE MESYLATE (PM) STORED AT 2-8° C.

| Time (weeks) | Concentration (mg/mL) | Percent of Initial PM Concentration Remaining (%) | Phentolamine Mesylate Area Percent (%) | pH |
|---|---|---|---|---|
| 0 | 10.520 | 100.0 | 99.63 | 5.001 |
| 1 | N/A | N/A | N/A | N/A |
| 2 | N/A | N/A | N/A | N/A |
| 4 | 9.860 | 93.4 | 99.65 | 6.460 |

TABLE 1B

1% (w/v) PHENTOLAMINE MESYLATE (PM) SOLUTION STORED AT 25° C.

| Time (weeks) | Concentration (mg/mL) | Percent of Initial PM Concentration Remaining (%) | Phentolamine Mesylate Area Percent (%) | pH |
|---|---|---|---|---|
| 0 | 10.520 | 100.0 | 99.63 | 5.001 |
| 1 | N/A | N/A | N/A | N/A |
| 2 | N/A | N/A | N/A | N/A |
| 4 | 9.630 | 91.60 | 98.85 | 6.360 |

TABLE 1C

1% (w/v) PHENTOLAMINE MESYLATE (PM) SOLUTION STORED AT 40° C.

| Time (weeks) | Concentration (mg/mL) | Percent of Initial PM Concentration Remaining (%) | Phentolamine Mesylate Area Percent (%) | pH |
|---|---|---|---|---|
| 0 | 10.520 | 100.0 | 99.63 | 5.001 |
| 1 | N/A | N/A | N/A | N/A |
| 2 | 9.913 | 94.20 | 99.41 | 5.034 |
| 4 | 9.370 | 89.10 | 97.20 | 6.400 |

TABLE 1D

1% (w/v) PHENTOLAMINE MESYLATE (PM) SOLUTION STORED AT 60° C.

| Time (weeks) | Concentration (mg/mL) | Percent of Initial PM Concentration Remaining (%) | Phentolamine Mesylate Area Percent (%) | pH |
|---|---|---|---|---|
| 0 | 10.520 | 100.0 | 99.63 | 5.001 |
| 1 | 8.723 | 87.20 | 89.53 | 6.006 |
| 2 | 8.544 | 81.20 | 91.86 | 5.406 |

As demonstrated by the data in Tables 1A-1D, phentolamine mesylate degrades rapidly in water over the brief period of 4 weeks across a wide range of temperatures.

Example 2—Stability of 1% (W/V) Phentolamine Mesylate and 5% (W/V) Mannitol in Water The purpose of this experiment was to examine stability of an aqueous solution containing phentolamine mesylate (1.0% w/v) and mannitol (500 w/v) at three temperatures: 2-8° C., 25° C., and 40° C. For clarity, the solutions tested in this example did not contain a buffer.

Experimental Design and Methods

Phentolamine mesylate (1.0% w/v) was obtained from Spectrum Pharmaceuticals. The HPLC analytical method for analysis of the formulations was developed by Newport Scientific, Inc.

The assay for API, impurities and degradants was performed using Atlantis HILIC 4.6 mm×250 mm×5 m column. The injection volume was 10 μL. Mobile phase A: 10 mM $HCOONH_4$ in water (12%). $HCOONH_4$ (10 mmol, 630 mg) was dissolved in 950 mL water. The pH was adjusted to 3.0 by addition of formic acid. The volume was then completed to 1 L by adding water (50 mL). Mobile phase B: Acetonitrile (88%). The temperature was 35° C., the flow rate was 1 mL/min, the injection volume was 10 μL and the sample/standard concentration was 100 μg/mL.

Each sample was well shaken and then 0.5 to 1.0 mL were transferred into a clear test tube and physical appearance recorded.

Bottles containing 5.0 mL of 1.0% w/v phentolamine mesylate ophthalmic solution were stored at 2-8° C., 25° C., and 40° C. For each tested time point, two bottles were used. Before testing, all samples were allowed to equilibrate to room temperature. Immediately prior to conducting each test, each sample was vigorously shaken. Then, assay for API, impurities and degradants was performed according to the method described above and the physical appearance of the sample was determined. Also, the pH of the sample was determined and measured in duplicate to ensure that there is no drift.

A final report was generated upon completion of the protocol.

An aqueous phentolamine mesylate (1.0% w/v) solution containing mannitol (5% w/v) was tested for stability over the course of twelve months at the following temperatures: 2-8° C., 25° C., and 40° C. For comparison purposes, an EDTA-containing solution was also prepared and tested. The EDTA-containing solution was identical to the above solution, except that the solution also contained 0.01% w/v EDTA.

Results

Figure 1B:
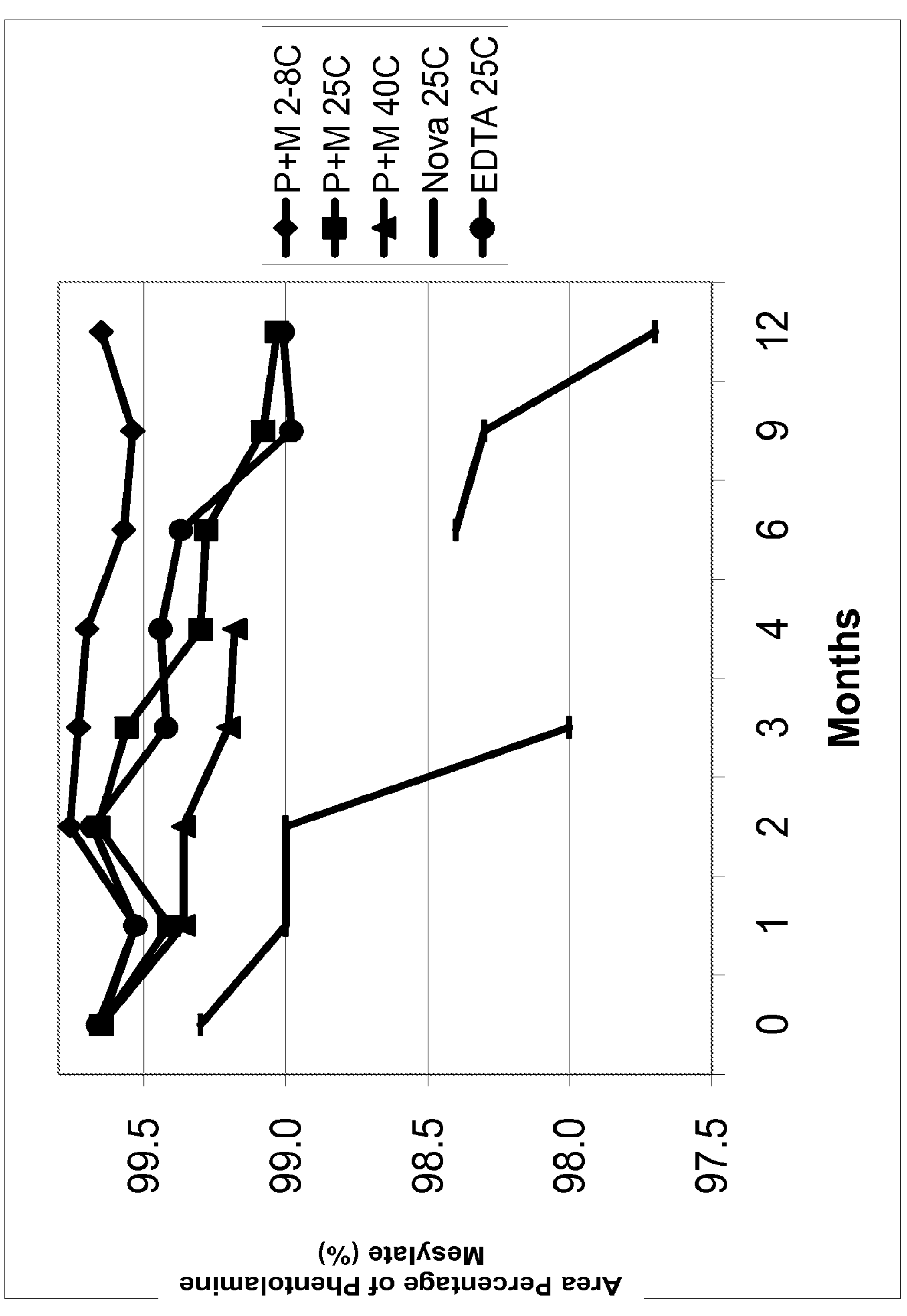
FIG. 1B is a line graph of area percent of phentolamine mesylate vs time for solutions stored at, for example, 2-8° C., 25° C., and 40° C.
Figure 1C:
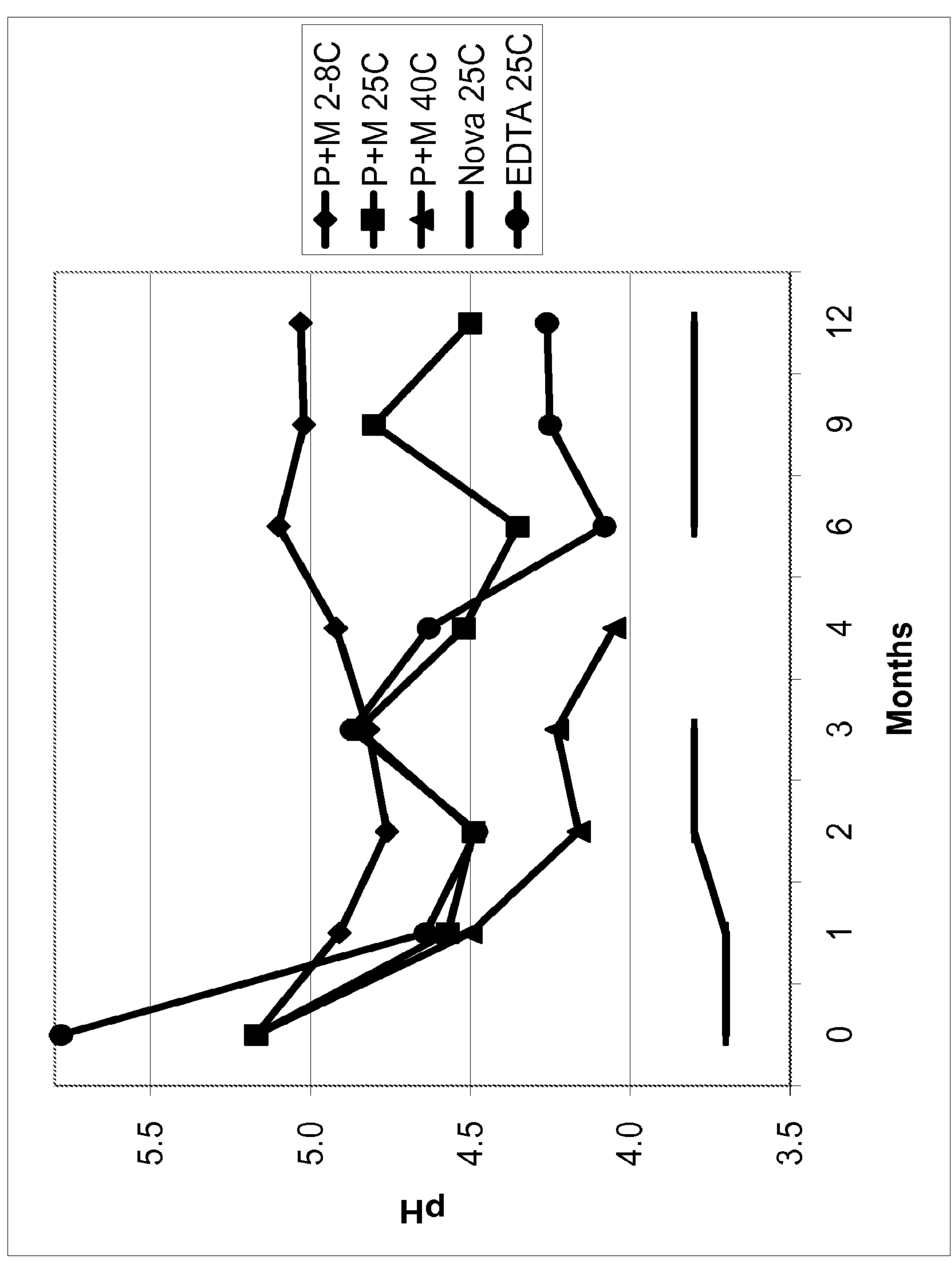
FIG. 1C is a line graph of pH of phentolamine mesylate solutions vs time for solutions stored at, for example, 2-8° C., 25° C., and 40° C.

The results of this experiment are demonstrated in Tables 2A-2F and in FIGS. 1A-1C.

TABLE 2A

1% (w/v) PHENTOLAMINE MESYLATE (PM) AND 5% (w/v) MANNITOL SOLUTION STORED AT 2-8° C.

| Time (months) | Concentration (mg/mL) | Percent of Initial PM Concentration (%) | Phentolamine Mesylate Area Percent (%) | pH |
|---|---|---|---|---|
| 0 | 10.01 | 100.0 | 99.65 | 5.17 |
| 1 | 10.17 | 101.64 | 99.53 | 4.91 |
| 2 | 10.00 | 99.84 | 99.76 | 4.76 |
| 3 | 9.79 | 97.84 | 99.73 | 4.82 |
| 4 | 10.02 | 100.07 | 99.70 | 4.92 |
| 6 | 10.18 | 101.67 | 99.57 | 5.03 |
| 9 | 10.02 | 100.14 | 99.54 | 5.02 |
| 12 | 10.34 | 103.37 | 99.65 | 5.03 |

TABLE 2B

1% (w/v) PHENTOLAMINE MESYLATE (PM) AND 5% (w/v) MANNITOL SOLUTION STORED AT 25° C., 40% RELATIVE HUMIDITY (RH)

| Time (months) | Concentration (mg/mL) | Percent of Initial PM Concentration (%) | Phentolamine Mesylate Area Percent (%) | pH |
|---|---|---|---|---|
| 0 | 10.01 | 100.0 | 99.65 | 5.17 |
| 1 | 10.25 | 102.38 | 99.41 | 4.57 |
| 2 | 9.84 | 98.33 | 99.66 | 4.49 |
| 3 | 9.88 | 98.68 | 99.56 | 4.85 |
| 4 | 10.24 | 102.24 | 99.3 | 4.52 |
| 6 | 10.22 | 102.09 | 99.28 | 4.35 |
| 9 | 9.89 | 98.80 | 99.08 | 4.80 |
| 12 | 10.63 | 106.26 | 99.03 | 4.50 |

TABLE 2C

1% (w/v) PHENTOLAMINE MESYLATE (PM) AND 5% (w/v) MANNITOL SOLUTION STORED AT 40° C.

| Time (months) | Concentration (mg/mL) | Percent of Initial PM Concentration (%) | Phentolamine Mesylate Area Percent (%) | pH |
|---|---|---|---|---|
| 0 | 10.01 | 100.0 | 99.65 | 5.17 |
| 0.5 | 9.90 | 98.88 | 99.59 | 5.95 |
| 1 | 9.84 | 98.29 | 99.36 | 4.50 |
| 2 | 9.85 | 98.34 | 99.36 | 4.16 |
| 3 | 9.70 | 96.91 | 99.20 | 4.23 |
| 4 | 9.99 | 99.80 | 99.18 | 4.05 |

TABLE 2D

1% (w/v) PHENTOLAMINE MESYLATE (PM), 5% (w/v) MANNITOL AND EDTA SOLUTION STORED AT 2-8° C.

| Time (months) | Concentration (mg/mL) | Percent of Initial PM Concentration (%) | Phentolamine Mesylate Area Percent (%) | pH |
|---|---|---|---|---|
| 0 | 10.01 | 100.0 | 99.66 | 5.78 |
| 1 | 10.05 | 100.42 | 99.77 | 4.77 |
| 2 | 10.02 | 100.08 | 99.75 | 4.68 |
| 3 | 9.80 | 97.95 | 99.75 | 4.83 |
| 4 | 10.01 | 100.02 | 99.49 | 4.60 |
| 6 | 10.12 | 101.07 | 99.45 | 4.66 |
| 9 | 10.05 | 100.39 | 99.60 | 4.85 |
| 12 | 10.20 | 102.01 | 99.57 | 4.71 |

TABLE 2E

1% (w/v) PHENTOLAMINE MESYLATE (PM), 5% (w/v) MANNITOL AND EDTA SOLUTION STORED AT 25° C., 40% RELATIVE HUMIDITY (RH)

| Time (months) | Concentration (mg/mL) | Percent of Initial PM Concentration (%) | Phentolamine Mesylate Area Percent (%) | pH |
|---|---|---|---|---|
| 0 | 10.01 | 100.0 | 99.66 | 5.78 |
| 1 | 10.19 | 101.78 | 99.53 | 4.64 |
| 2 | 9.93 | 99.19 | 99.68 | 4.48 |
| 3 | 9.81 | 98.01 | 99.42 | 4.87 |
| 4 | 10.18 | 101.73 | 99.44 | 4.63 |
| 6 | 10.15 | 101.44 | 99.37 | 4.08 |
| 9 | 10.12 | 101.08 | 98.98 | 4.25 |
| 12 | 10.55 | 105.46 | 99.01 | 4.26 |

TABLE 2F

1% (w/v) PHENTOLAMINE MESYLATE (PM), 5% (w/v) MANNITOL AND EDTA SOLUTION STORED AT 40° C.

| Time (months) | Concentration (mg/mL) | Percent of Initial PM Concentration (%) | Phentolamine Mesylate Area Percent (%) | pH |
|---|---|---|---|---|
| 0 | 10.01 | 100.0 | 99.66 | 5.78 |
| 0.5 | 9.90 | 98.88 | 99.56 | 4.70 |
| 1 | 9.79 | 97.83 | 99.39 | 4.56 |
| 2 | 9.74 | 97.34 | 99.41 | 4.15 |
| 3 | 10.01 | 99.99 | 99.14 | 4.39 |
| 4 | 9.93 | 99.23 | 98.98 | 4.51 |

For comparison purposes, Applicants have compared these results with the results obtained for a representative prior art formulation of phentolamine mesylate containing a metal chelator (Formulation #1 in Example 2 of U.S. Pat. No. 7,229,630 B2 (the '630 patent)) stored at 25° C. This prior art formulation is referred to as the "Nova Formulation" and contains 0.1 mg/mL (i.e., 0.01% w/v) phentolamine mesylate, 0.5 mg/mL (i.e., 0.05% w/v) disodium EDTA, 5% w/v d-mannitol, 10 mM sodium acetate, and water. Data points for the Nova Formulation were taken from Tables VII-IX of the '630 patent.

The terms "Phentolamine Area Percent" and "area percent" refer to an HPLC method of determining purity of the recovered phentolamine at each given time point by calculating the peak area. It is well known in the art how to calculate area percent.

FIG. 1A is a line graph of percentage of initial concentration of phentolamine mesylate remaining vs time. The five lines in the graph correspond to the five solutions tested: (1) solution containing phentolamine mesylate and mannitol (abbreviated P+M) stored at 2-8° C.; (2) solution containing phentolamine mesylate and mannitol (abbreviated P+M) stored at 25° C.; (3) solution containing phentolamine mesylate and mannitol (abbreviated P+M) stored at 40° C.; (4) the Nova Formulation stored at 25° C. (abbreviated as "Nova 25C"); and (5) solution containing phentolamine mesylate, mannitol, and EDTA stored at 25° C.

FIG. 1B is a line graph of area percent of phentolamine mesylate vs time. The five lines in the graph correspond to the five solutions tested: (1) solution containing phentolamine mesylate and mannitol (abbreviated P+M) stored at 2-8° C.; (2) solution containing phentolamine mesylate and mannitol (abbreviated P+M) stored at 25° C.; (3) solution containing phentolamine mesylate and mannitol (abbreviated P+M) stored at 40° C.; (4) the Nova Formulation stored at 25° C. (abbreviated as "Nova 25C"); and (5) solution containing phentolamine mesylate, mannitol, and EDTA stored at 25° C.

FIG. 1C is a line graph of pH of the phentolamine mesylate solution vs time. The five lines in the graph correspond to the five solutions tested: (1) solution containing phentolamine mesylate and mannitol (abbreviated P+M) stored at 2-8° C.; (2) solution containing phentolamine mesylate and mannitol (abbreviated P+M) stored at 25° C.; (3) solution containing phentolamine mesylate and mannitol (abbreviated P+M) stored at 40° C.; (4) the Nova Formulation stored at 25° C. (abbreviated as "Nova 25C"); and (5) solution containing phentolamine mesylate, mannitol, and EDTA stored at 25° C.

As the data in Tables 2A-2F and FIGS. 1A-1B indicated, the solution containing 1% (w/v) phentolamine mesylate and 5% mannitol is very stable over time as measured by both percent initial concentration and area percent. In fact, the formulation has superior stability than conventional Nova 25C formulation containing a metal chelator (EDTA). The absence of EDTA in the inventive formulation did not have a negative effect on either percentage of initial concentration of phentolamine mesylate or area percent of phentolamine.

FIG. 1C shows that the pH of the tested formulations at 25° C. and 40° C. tends to slightly decline over time. These tested formulations did not include a buffer.

Example 3—Stability of 0.01% W/V and 2.0% w/v Phentolamine Mesylate and 5% w/v Mannitol in Water The purpose of this experiment was to examine the stability of aqueous solutions containing 0.01% w/v or 2.0% w/v phentolamine mesylate and 5% w/v mannitol (without a buffer) at two temperatures (25° C. and 40° C.) to determine if the concentration of phentolamine mesylate effects stability.

Experimental Design and Methods

Aqueous solutions containing phentolamine mesylate (0.01% or 2.0% w/v) and mannitol (5% w/v) were tested for stability over the course of twelve months at 25° C. and 40° C.

The experimental design and methods were substantially similar to those of the experiment described in Examples 1 and 2 above.

Results

Figure 2A:
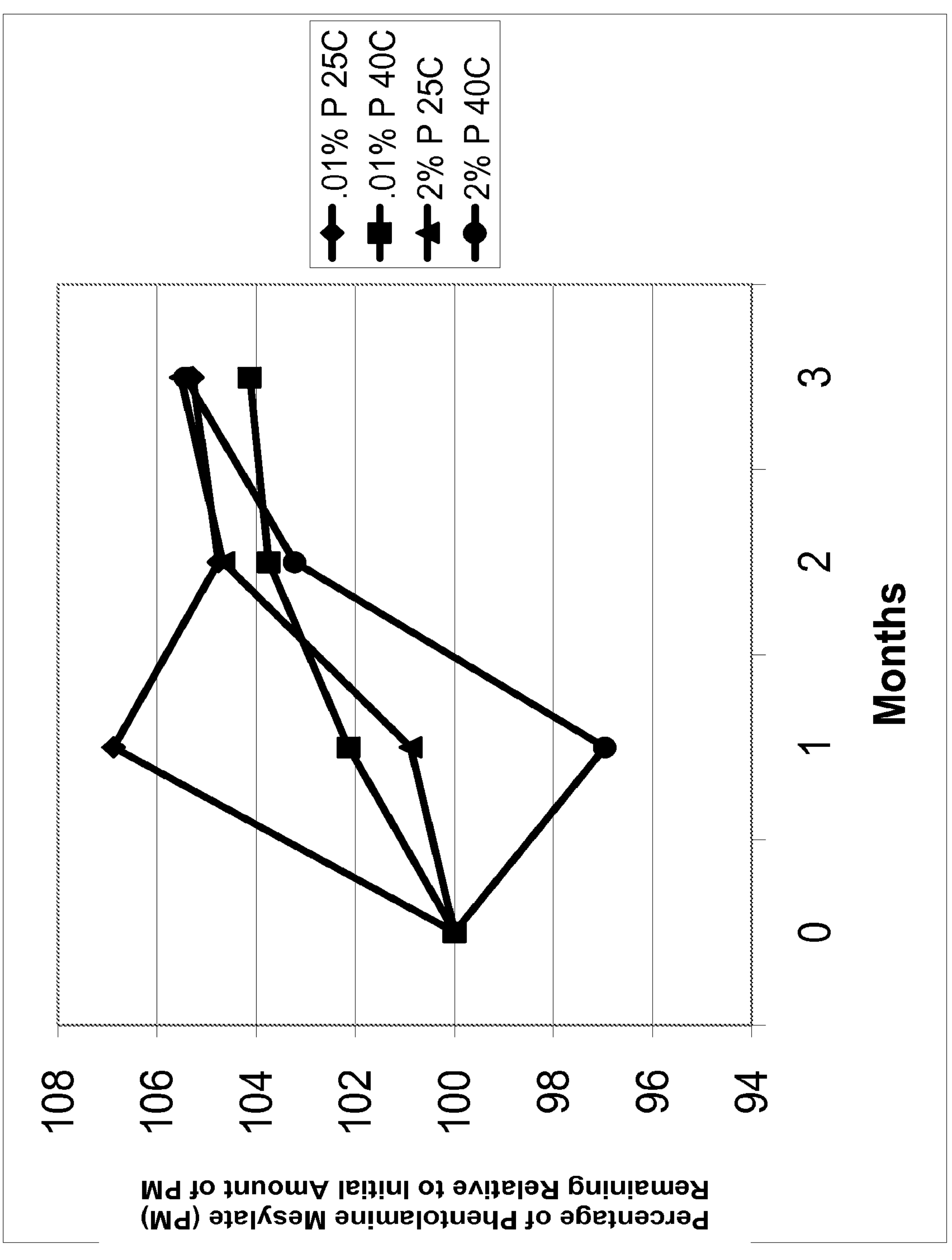
FIG. 2A is a line graph of percent of initial concentration of phentolamine mesylate vs time for solutions containing 0.01% w/v phentolamine mesylate and solutions containing 2% w/v phentolamine mesylate stored at either 25° C. or 40° C.
Figure 2B:
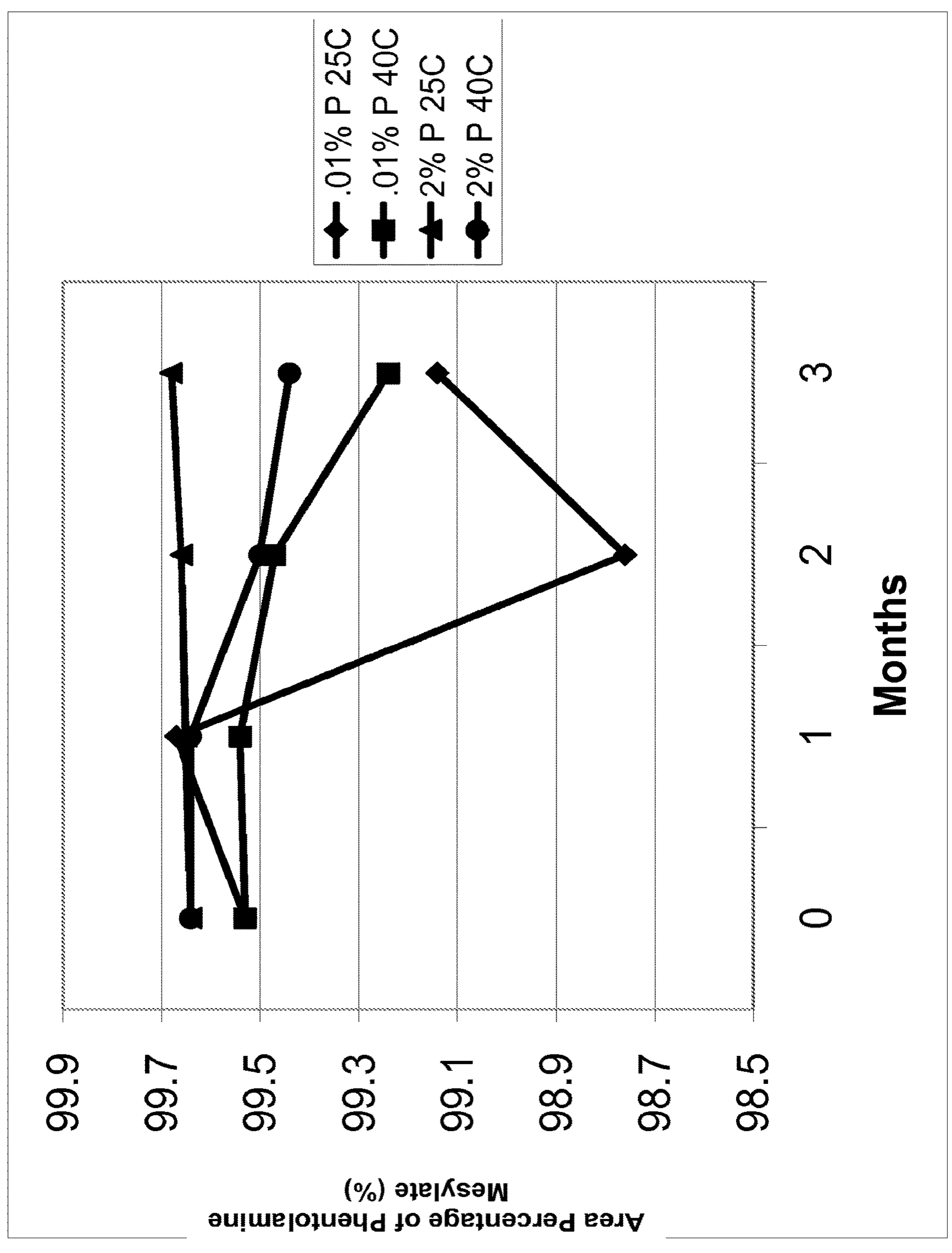
FIG. 2B is a line graph of area percent of phentolamine mesylate vs time for solutions containing 0.01% w/v phentolamine mesylate and solutions containing 2% w/v phentolamine mesylate stored at either 25° C. or 40° C.
Figure 2C:
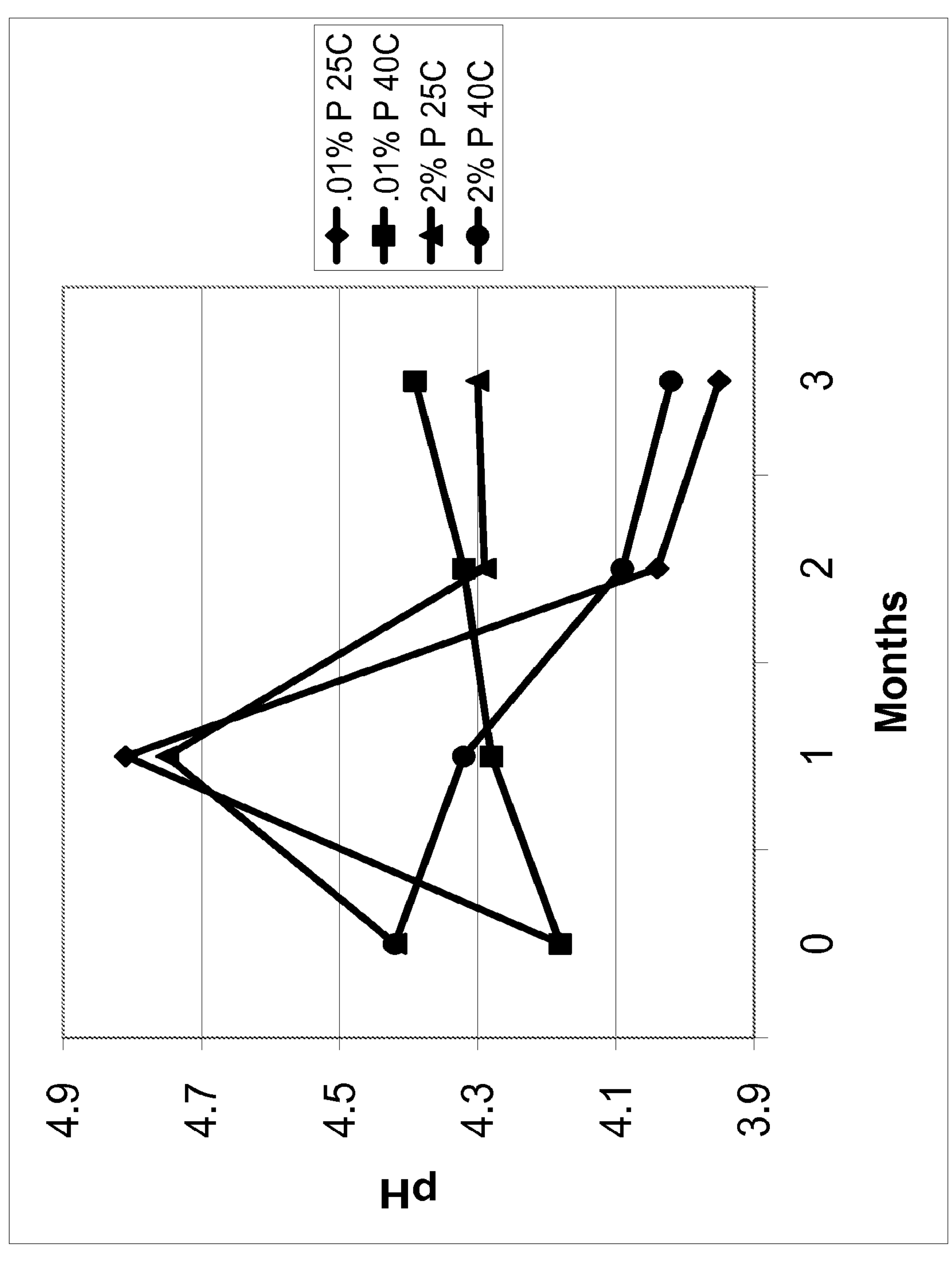
FIG. 2C is a line graph of pH of the phentolamine mesylate solutions vs time for solutions containing 0.01% w/v phentolamine mesylate and solutions containing 2% phentolamine mesylate stored at either 25° C. or 40° C.

The results of this experiment are provided in Tables 3A-D and in FIGS. 2A-2C.

TABLE 3A

2% (w/v) PHENTOLAMINE MESYLATE (PM) AND 5% (w/v) MANNITOL SOLUTIONS STORED AT 25° C., 40% RH

| Time (months) | Concentration (mg/mL) | Percent of Initial PM Concentration (%) | Phentolamine Mesylate Area Percent (%) | pH |
|---|---|---|---|---|
| 0 | 19.85 | 100.0 | 99.64 | 4.42 |
| 1 | 20.03 | 100.88 | 99.65 | 4.75 |
| 2 | 20.78 | 104.67 | 99.66 | 4.29 |
| 3 | 20.95 | 105.52 | 99.68 | 4.30 |

TABLE 3B

2% (w/v) PHENTOLAMINE MESYLATE (PM) AND 5% (w/v) MANNITOL SOLUTIONS STORED AT 40° C.

| Time (months) | Concentration (mg/mL) | Percent of Initial PM Concentration (%) | Phentolamine Mesylate Area Percent (%) | pH |
|---|---|---|---|---|
| 0 | 19.85 | 100.0 | 99.64 | 4.42 |
| 1 | 19.25 | 96.96 | 99.64 | 4.32 |
| 2 | 20.49 | 103.22 | 99.50 | 4.09 |
| 3 | 20.93 | 105.43 | 99.44 | 4.02 |

TABLE 3C 0.01% (w/v) PHENTOLAMINE MESYLATE (PM) AND 5% (w/v) MANNITOL SOLUTIONS STORED AT 25° C.

| Time (months) | Concentration (mg/mL) | Percent of Initial PM Concentration (%) | Phentolamine Mesylate Area Percent (%) | pH |
|---|---|---|---|---|
| 0 | 0.093 | 100.0 | 99.53 | 4.18 |
| 1 | 0.100 | 106.88 | 99.67 | 4.81 |
| 2 | 0.098 | 104.76 | 98.76 | 4.04 |
| 3 | 0.098 | 105.28 | 99.14 | 3.95 |

TABLE 3D 0.01% (w/v) PHENTOLAMINE MESYLATE (PM) AND 5% (w/v) MANNITOL SOLUTIONS STORED AT 40° C.

| Time (months) | Concentration (mg/mL) | Percent of Initial PM Concentration (%) | Phentolamine Mesylate Area Percent (%) | pH |
|---|---|---|---|---|
| 0 | 0.093 | 100.0 | 99.53 | 4.18 |
| 1 | 0.095 | 102.13 | 99.54 | 4.28 |
| 2 | 0.097 | 103.74 | 99.47 | 4.32 |
| 3 | 0.097 | 104.13 | 99.24 | 4.39 |

FIG. 2A shows a line graph of percent of initial concentration of phentolamine mesylate remaining vs time. FIG. 2B shows a line graph of area percent of phentolamine mesylate vs time. FIG. 2C shows a line graph of pH of the phentolamine mesylate solution vs time. In each of FIGS. 2A, 2B, and 2C, the four lines in the graphs correspond to the four solutions tested: (1) solution containing phentolamine mesylate (0.01% w/v) and mannitol (abbreviated 0.01% P) stored at 25° C.; (2) solution containing phentolamine mesylate (0.01% w/v) and mannitol (abbreviated 0.1% P) stored at 40° C.; (3) solution containing phentolamine mesylate (2% w/v) and mannitol (abbreviated 2% P) stored at 25° C.; (4) solution containing phentolamine mesylate (2% w/v) and mannitol (abbreviated 2% P) stored at 40° C.

As the data in Tables 3A-3D and FIGS. 2A-2B show, there is no significant difference in the stability profile between the solutions tested containing 0.01% w/v and 2.0% w/v phentolamine mesylate. The data in FIG. 2C shows that the pH of the solutions at 25° C. and 40° C. declined slightly over time. These tested solutions did not include a buffer.

Example 4—Stability of 1% (W/v) Phentolamine Mesylate, 4% (W/v) Mannitol and 3 mM Sodium Acetate Buffer in Water The purpose of this experiment was to examine whether adding a weak buffer further stabilizes the phentolamine mesylate/mannitol solution by preventing or reducing the slight decline in pH over time as observed in non-buffered solutions (See, Examples 2 and 3 above). Sodium acetate was used as a weak buffer at a concentration of 3 mM. In one tested solution, hydroxypropyl methylcellulose (HPMC) was added to the solution. Stability of the solutions was tested at three temperatures: 2-8° C., 25° C., and 40° C.

Experimental Design and Methods

An aqueous solution containing phentolamine mesylate (1.0% w/v), mannitol (4% w/v), and sodium acetate buffer (3 mM) with and without HPMC was tested for stability over the course of six months at the following temperatures: 2-8° C., 25° C., and 40° C.

The experimental design and methods were substantially similar to those of the experiment described in Examples 1 and 2 above.

Results

The results of this experiment are shown in Tables 4A-4F and in FIGS. 3A-3F.

TABLE 4A

1% (w/v) PHENTOLAMINE MESYLATE (PM), 4% (w/v) MANNITOL AND 3 mM SODIUM ACETATE BUFFER (NO HPMC) SOLUTION STORED AT 2-8° C.

| Time (months) | Concentration (mg/mL) | Percent of Initial PM Concentration (%) | Phentolamine Mesylate Area Percent (%) | pH |
|---|---|---|---|---|
| 0 | 9.65 | 100.0 | 98.73 | 4.81 |
| 3 | 10.59 | 109.74 | 99.67 | 4.87 |
| 6 | 10.45 | 108.29 | 99.31 | 4.94 |

TABLE 4B

1% (w/v) PHENTOLAMINE MESYLATE (PM), 4% (w/v) MANNITOL AND 3 mM SODIUM ACETATE BUFFER (NO HPMC) SOLUTION STORED AT 25° C.

| Time (months) | Concentration (mg/mL) | Percent of Initial PM Concentration (%) | Phentolamine Mesylate Area Percent (%) | pH |
|---|---|---|---|---|
| 0 | 9.65 | 100.0 | 98.73 | 4.81 |
| 1 | 10.32 | 106.94 | 99.32 | 4.97 |
| 2 | 10.55 | 109.33 | 99.49 | 4.94 |
| 3 | 10.54 | 109.22 | 99.34 | 4.89 |
| 6 | 10.4 | 107.77 | 98.90 | 4.78 |

TABLE 4C

1% (w/v) PHENTOLAMINE MESYLATE (PM), 4% (w/v) MANNITOL AND 3 mM SODIUM ACETATE BUFFER (NO HPMC) SOLUTION STORED AT 40° C.

| Time (months) | Concentration (mg/mL) | Percent of Initial PM Concentration (%) | Phentolamine Mesylate Area Percent (%) | pH |
|---|---|---|---|---|
| 0 | 9.65 | 100.0 | 98.73 | 4.81 |
| 2 weeks | 9.83 | 101.87 | 99.36 | 4.93 |
| 1 | 9.76 | 101.14 | 97.90 | 4.89 |
| 2 | 10.52 | 109.02 | 97.22 | 4.93 |
| 3 | 10.02 | 103.83 | 96.09 | 4.77 |
| 6 | 9.26 | 95.96 | 92.52 | 4.82 |

TABLE 4D

1% (W/V) PHENTOLAMINE MESYLATE (PM), 4% (w/v) MANNITOL AND 3 mM SODIUM ACETATE BUFFER (WITH HPMC) SOLUTION STORED AT 2-8° C.

| Time (months) | Concentration (mg/mL) | Percent of Initial PM Concentration (%) | Phentolamine Mesylate Area Percent (%) | P H |
|---|---|---|---|---|
| 0 | 9.56 | 100.0 | 98.73 | 4.86 |
| 3 | 10.12 | 105.86 | 99.70 | 4.75 |
| 6 | 10.16 | 106.28 | 99.49 | 4.84 |

TABLE 4E

1% (W/V) PHENTOLAMINE MESYLATE (PM), 4% (w/v) MANNITOL AND 3 mM SODIUM ACETATE BUFFER (WITH HPMC) SOLUTION STORED AT 25° C.

| Time (months) | Concentration (mg/mL) | Percent of Initial PM Concentration (%) | Phentolamine Mesylate Area Percent (%) | pH |
|---|---|---|---|---|
| 0 | 9.56 | 100.0 | 98.73 | 4.86 |
| 1 | 10.02 | 104.81 | 99.23 | 4.81 |
| 2 | 10.21 | 106.80 | 99.50 | 4.93 |
| 3 | 9.11 | 95.29 | 99.34 | 4.76 |
| 6 | 9.91 | 103.69 | 99.06 | 4.71 |

TABLE 4F

1% (W/V) PHENTOLAMINE MESYLATE (PM), 4% (w/v) MANNITOL AND 3 mM SODIUM ACETATE BUFFER (WITH HPMC) SOLUTION STORED AT 40° C.

| Time (months) | Concentration (mg/mL) | Percent of Initial PM Concentration (%) | Phentolamine Mesylate Area Percent (%) | pH |
|---|---|---|---|---|
| 0 | 9.56 | 100.0 | 98.73 | 4.86 |
| 2 weeks | 9.88 | 103.35 | 99.37 | 4.83 |
| 1 | 10.02 | 104.81 | 98.34 | 4.83 |
| 2 | 10.05 | 105.13 | 97.69 | 4.84 |
| 3 | 9.52 | 99.58 | 96.62 | 4.79 |
| 6 | 9.39 | 98.22 | 94.36 | 4.64 |

For comparison purposes, the results are compared with the results obtained for the Nova formulation stored at 25° C.

Figure 3A:
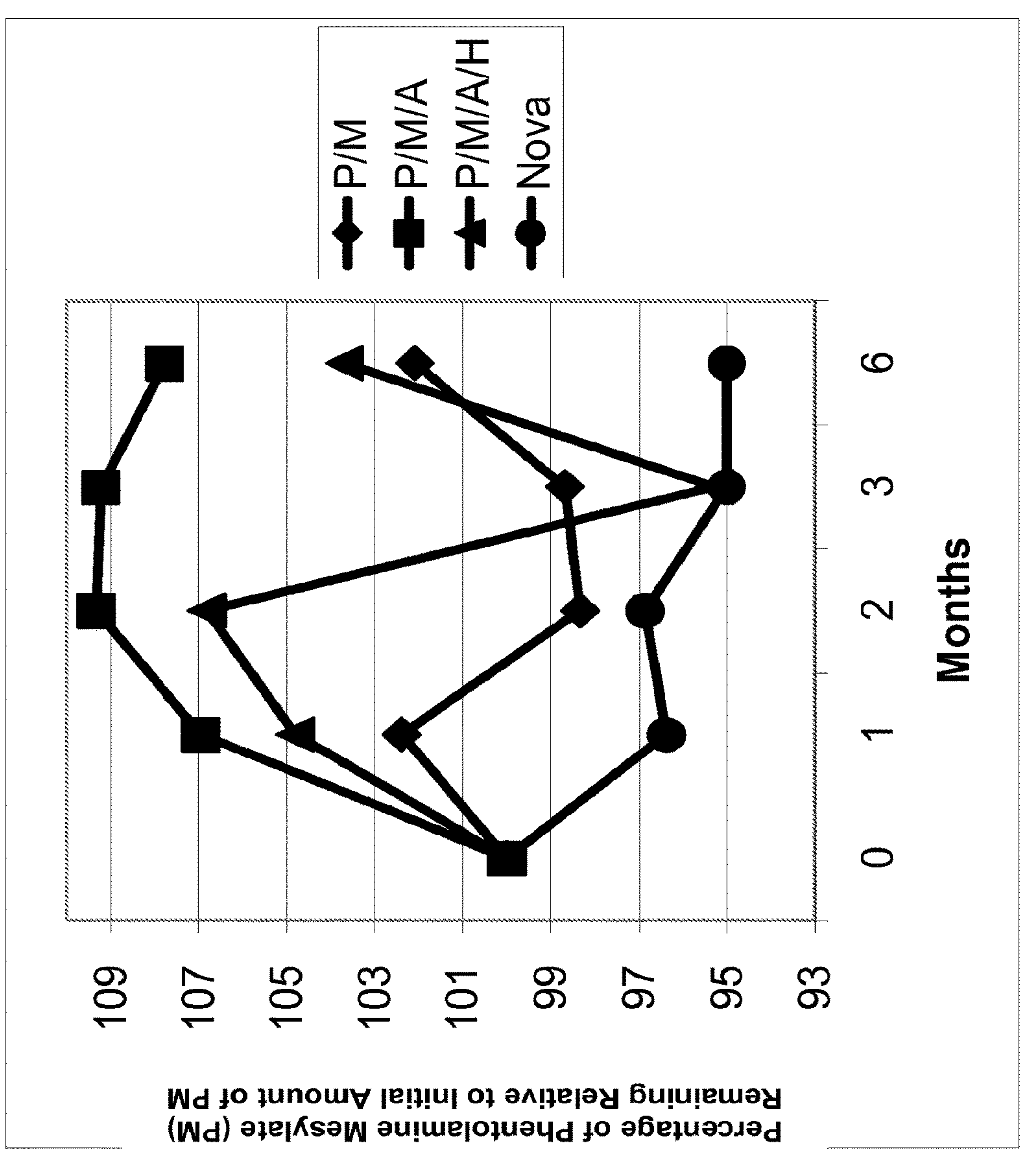
FIG. 3A is a line graph of percent of initial concentration of phentolamine mesylate remaining vs time for solutions stored at 25° C. containing (i) phentolamine mesylate and mannitol (abbreviated P/M); (2) phentolamine mesylate, mannitol and acetate buffer without HPMC (abbreviated P/M/A); (3) phentolamine mesylate, mannitol and acetate buffer with HPMC (abbreviated P/M/A/H); and (4) the Nova Formulation (identified as "Nova" in the figure legend).
Figure 3B:
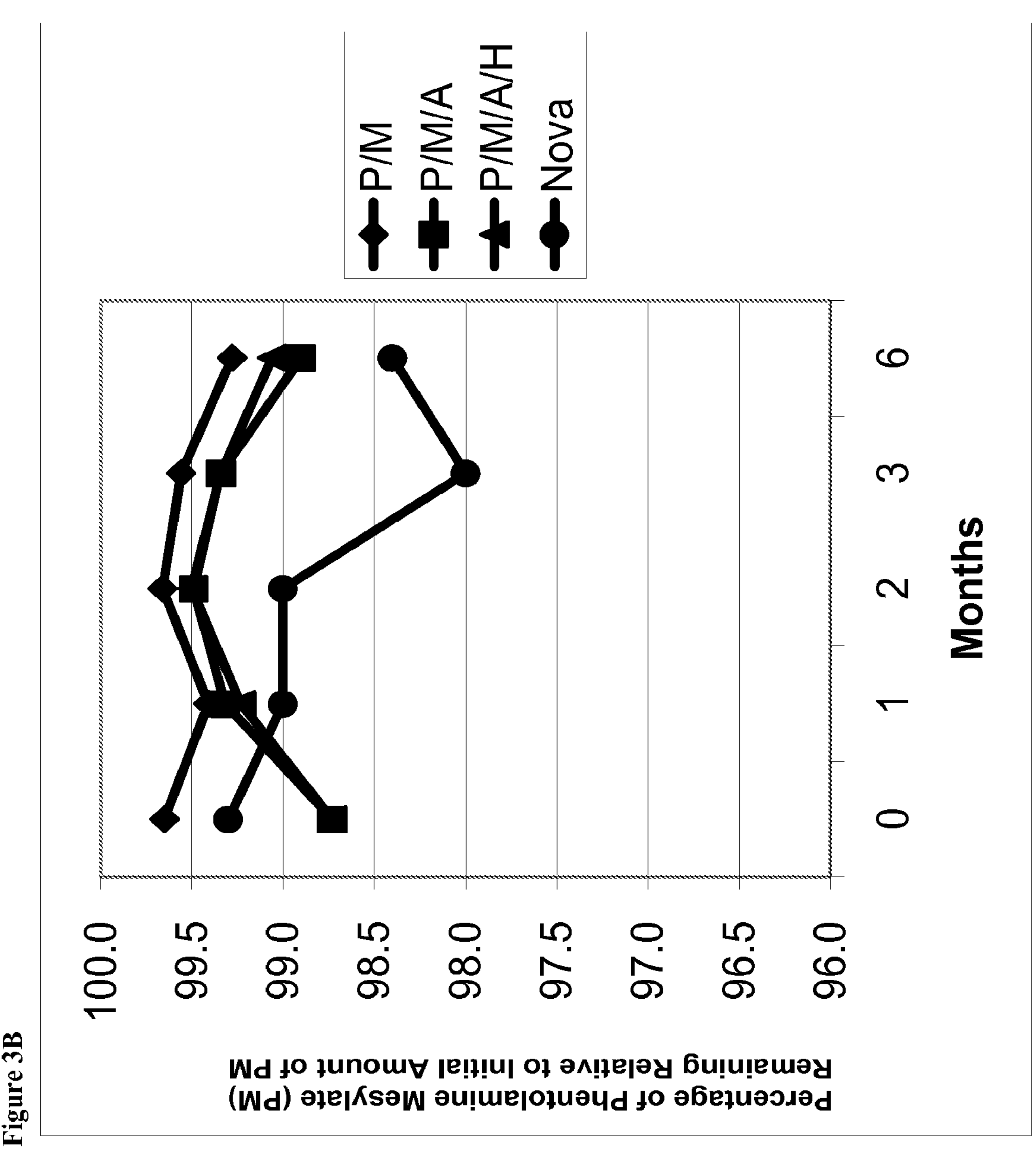
FIG. 3B is a line graph of area percent of phentolamine mesylate vs time for solutions stored at 25° C. containing (i) phentolamine mesylate and mannitol (abbreviated P/M); (2) phentolamine mesylate, mannitol and acetate buffer without HPMC (abbreviated P/M/A); (3) phentolamine mesylate, mannitol and acetate buffer with HPMC (abbreviated P/M/A/H); or (4) the Nova Formulation (identified as "Nova" in the figure legend).
Figure 3C:
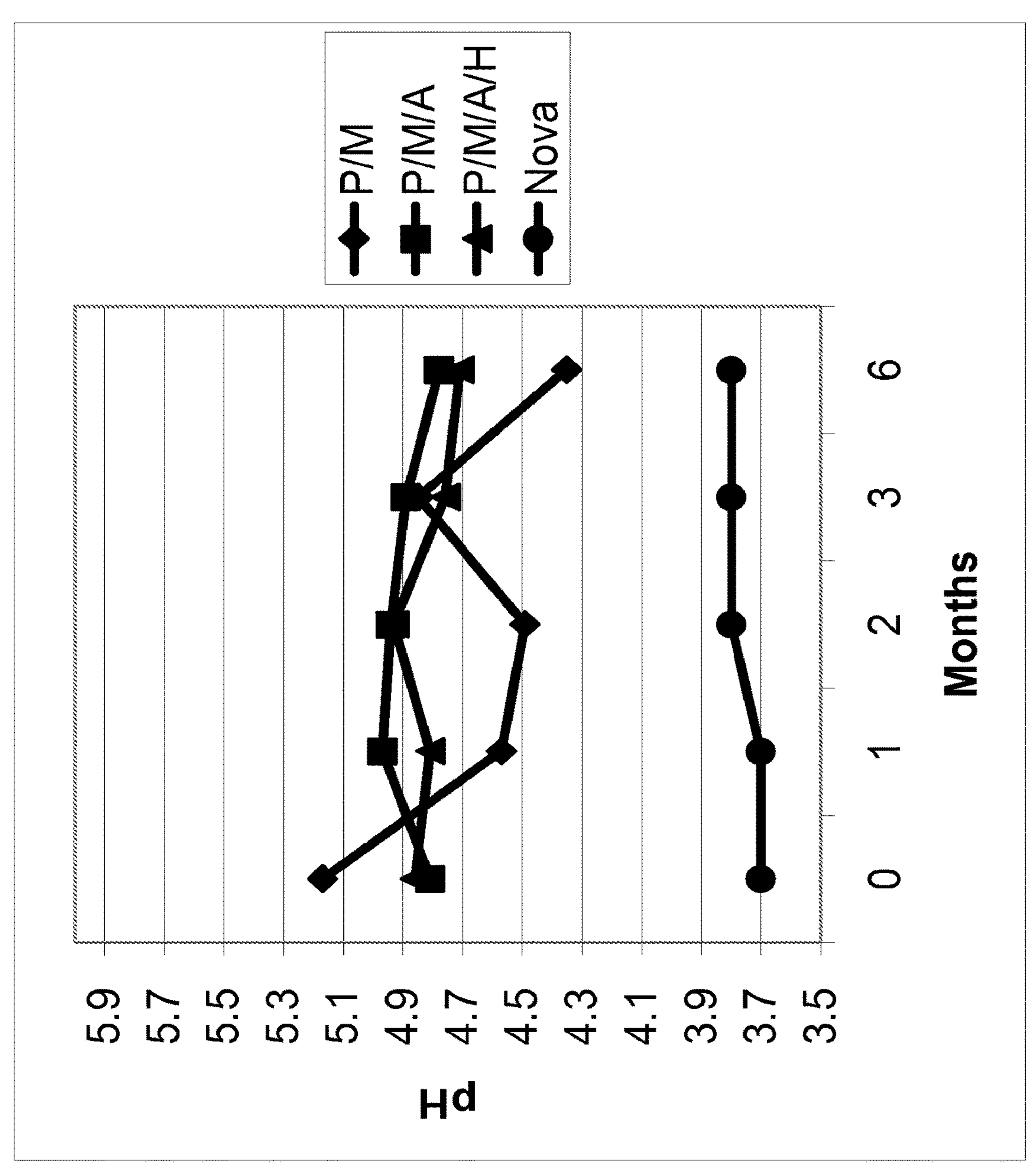
FIG. 3C is a line graph of pH of the phentolamine mesylate solution vs time for solutions stored at 25° C. and containing (1) phentolamine mesylate and mannitol (abbreviated P/M); (2) phentolamine mesylate, mannitol and acetate buffer without HPMC (abbreviated P/M/A); (3) phentolamine mesylate, mannitol and acetate buffer with HPMC (abbreviated P/M/A/H); or (4) the Nova Formulation (identified as "Nova" in the figure legend).

FIG. 3A shows a line graph of percentage of initial concentration of phentolamine mesylate remaining at 25° C. vs time. FIG. 3B shows a line graph of area percent of phentolamine mesylate vs time at 25° C. FIG. 3C shows a line graph of pH of the phentolamine mesylate solution vs time at 25° C. In each of FIGS. 3A to 3C, the four lines in the graphs correspond to the four solutions tested: (1) phentolamine mesylate and mannitol (abbreviated P/M); (2) phentolamine mesylate, mannitol and acetate buffer without IPMC (abbreviated P/M/A); (3) phentolamine mesylate, mannitol and acetate buffer with IPMC (abbreviated P/M/A/H); and (4) the Nova Formulation (abbreviated "Nova").

Figure 3E:
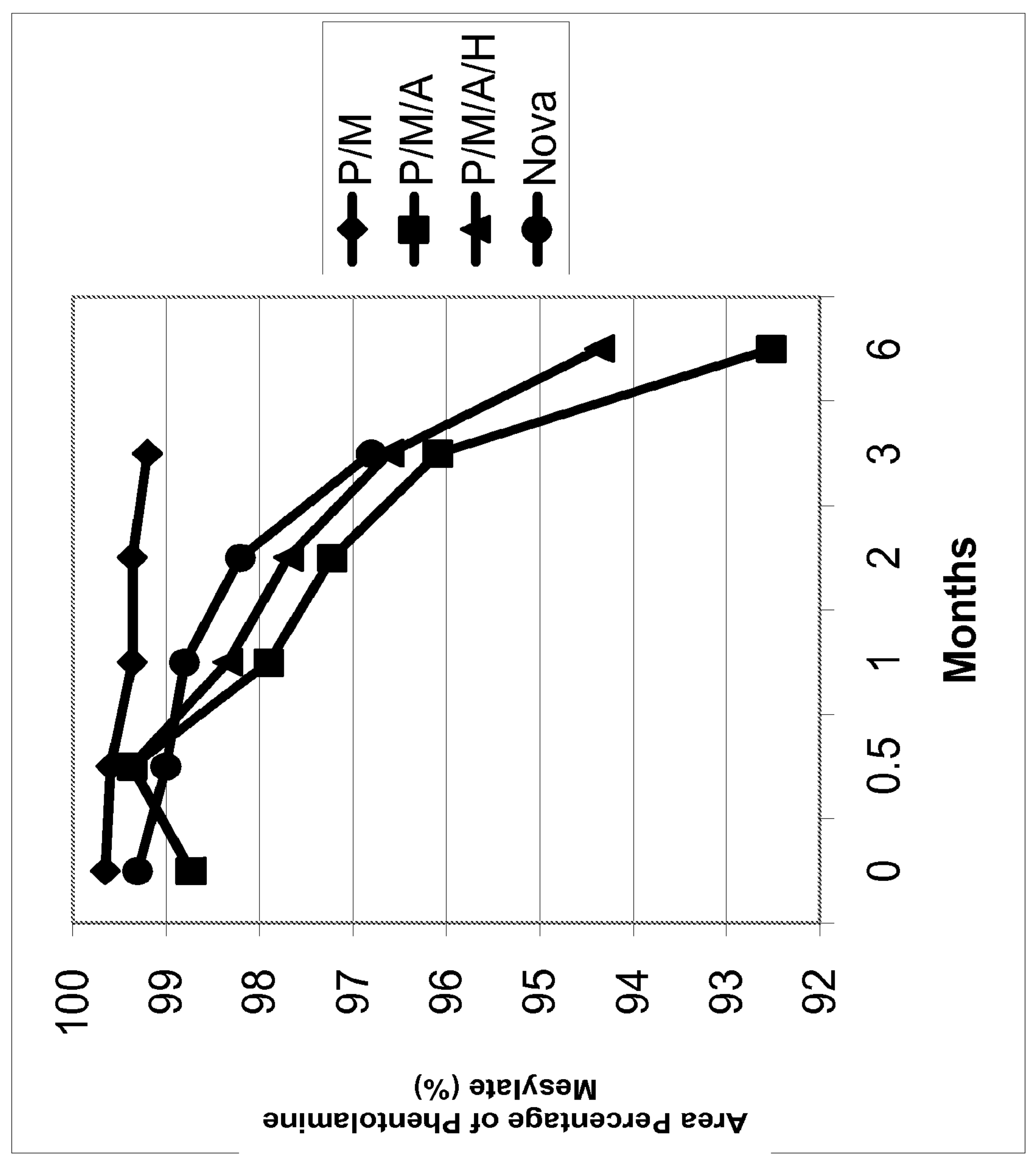
FIG. 3E is a line graph of area percent of phentolamine mesylate vs time for solutions stored at 40° C. containing (1) phentolamine mesylate and mannitol (abbreviated P/M); (2) phentolamine mesylate, mannitol and acetate buffer without HPMC (abbreviated P/M/A); (3) phentolamine mesylate, mannitol and acetate buffer with HPMC (abbreviated P/M/A/H); or (4) the Nova Formulation (identified as "Nova" in the figure legend).
Figure 3F:
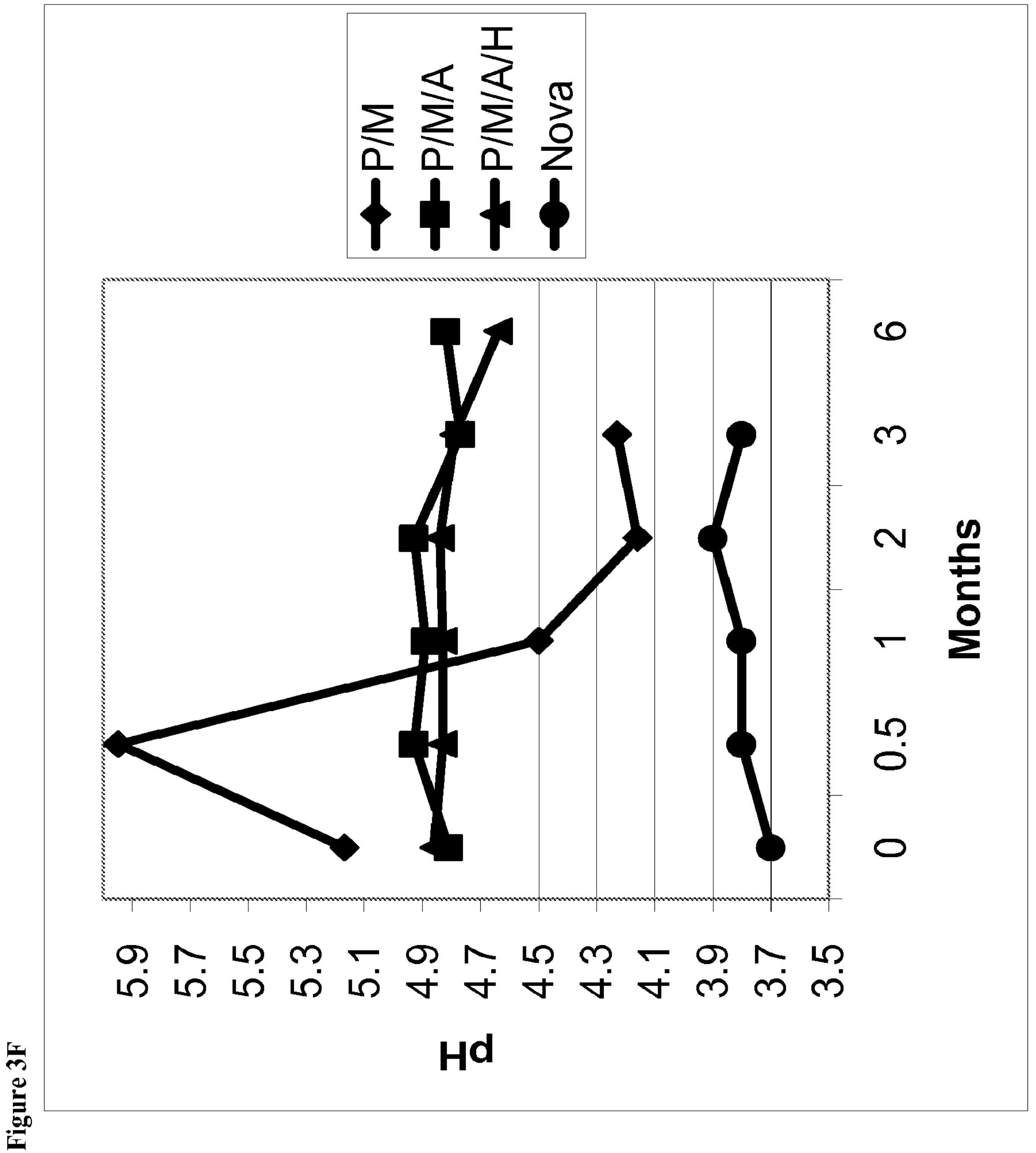
FIG. 3F is a line graph of pH of the phentolamine mesylate solution vs time for solutions stored at 40° C. containing (1) phentolamine mesylate and mannitol (abbreviated P/M); (2) phentolamine mesylate, mannitol and acetate buffer without HPMC (abbreviated P/M/A); (3) phentolamine mesylate, mannitol and acetate buffer with HPMC (abbreviated P/M/A/H); or (4) the Nova Formulation (identified as "Nova" in the figure legend).

FIG. 3D shows a line graph of percentage of initial concentration of phentolamine mesylate remaining at 40° C. vs time. FIG. 3E shows a line graph of area percent of phentolamine mesylate vs time at 40° C. FIG. 3F shows a line graph of pH of the phentolamine mesylate solution vs time at 40° C. In each of FIGS. 3D to 3F, the four lines in the graphs correspond to the four solutions tested: (1) a solution containing phentolamine mesylate and mannitol (abbreviated P/M); (2) a solution containing phentolamine mesylate, mannitol, and acetate buffer without IPMC (abbreviated P/M/A); (3) a solution containing phentolamine mesylate, mannitol and acetate buffer with IPMC (abbreviated P/M/A/H); and (4) the Nova Formulation (abbreviated "Nova").

Figure 3G:
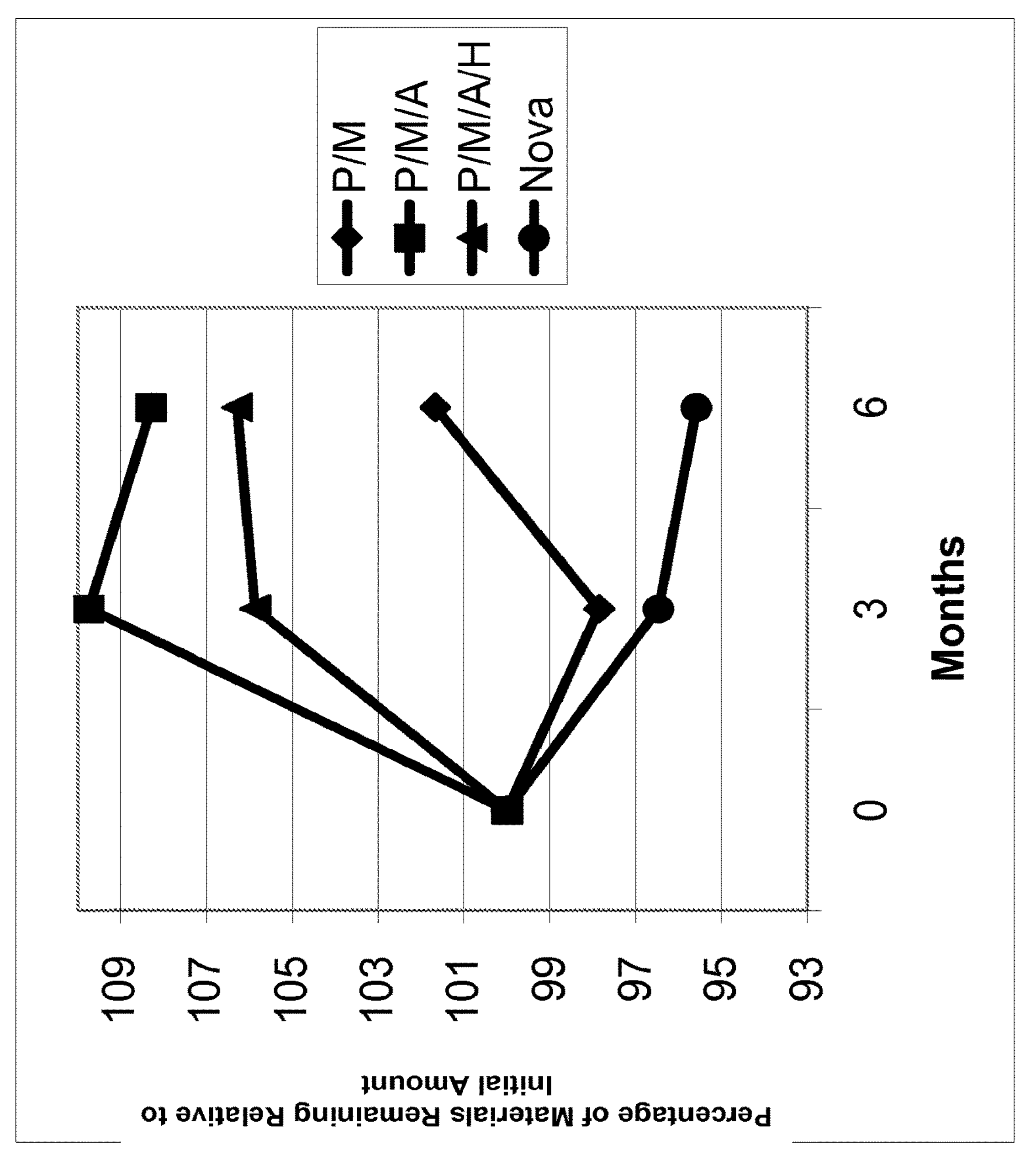
FIG. 3G is a line graph of percent of initial concentration of phentolamine mesylate remaining vs time for solutions stored at 2-8° C. containing (1) phentolamine mesylate and mannitol (abbreviated P/M); (2) phentolamine mesylate, mannitol and acetate buffer without HPMC (abbreviated P/M/A); (3) phentolamine mesylate, mannitol and acetate buffer with HPMC (abbreviated P/M/A/H); or (4) the Nova Formulation (identified as "Nova" in the figure legend).
Figure 3H:
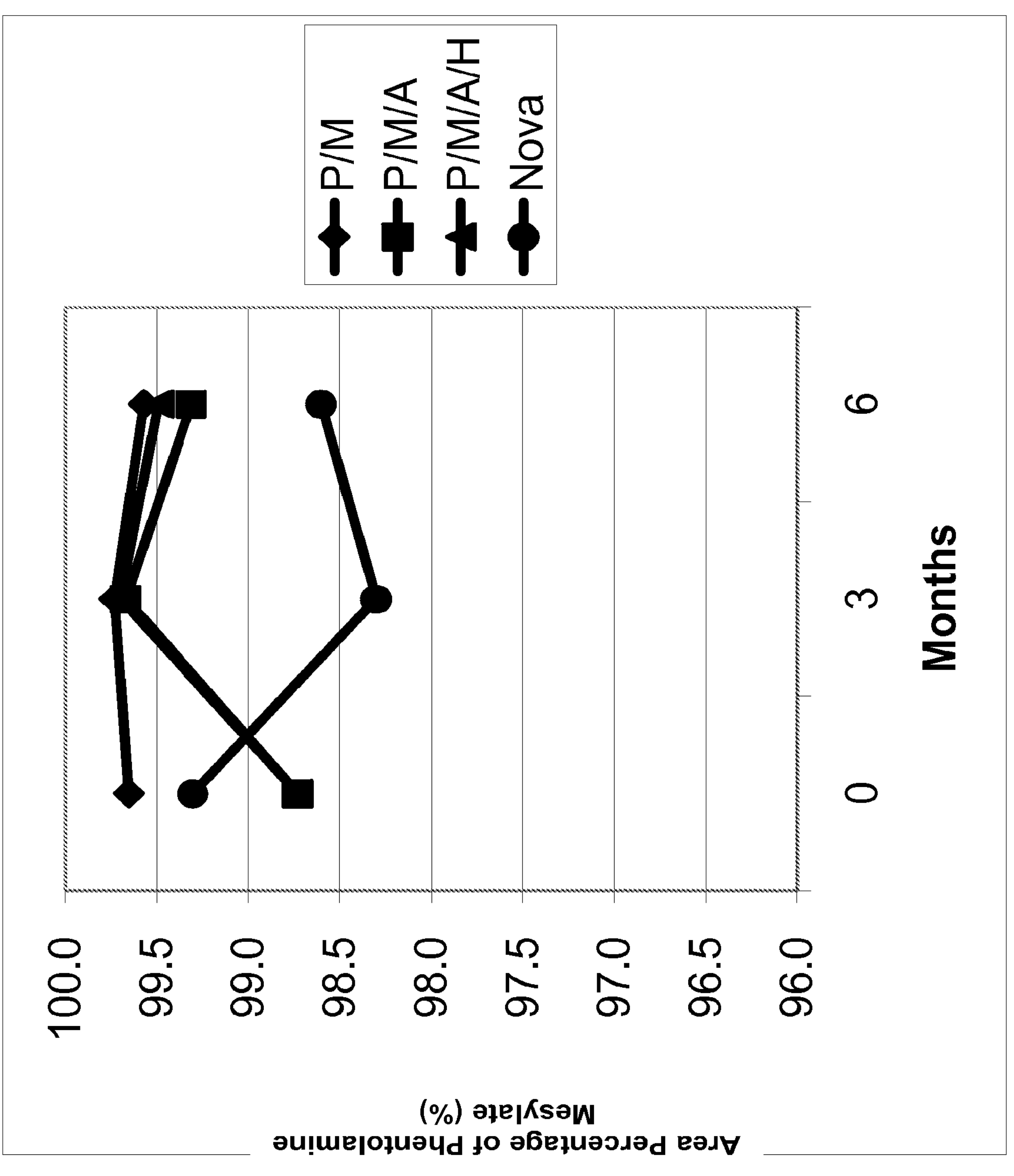
FIG. 3H is a line graph of area percent of phentolamine mesylate vs time for solutions stored at 2-8° C. containing (1) phentolamine mesylate and mannitol (abbreviated P/M); (2) phentolamine mesylate, mannitol and acetate buffer without HPMC (abbreviated P/M/A); (3) phentolamine mesylate, mannitol and acetate buffer with HPMC (abbreviated P/M/A/H); or (4) the Nova Formulation (identified as "Nova" in the figure legend).
Figure 3I:
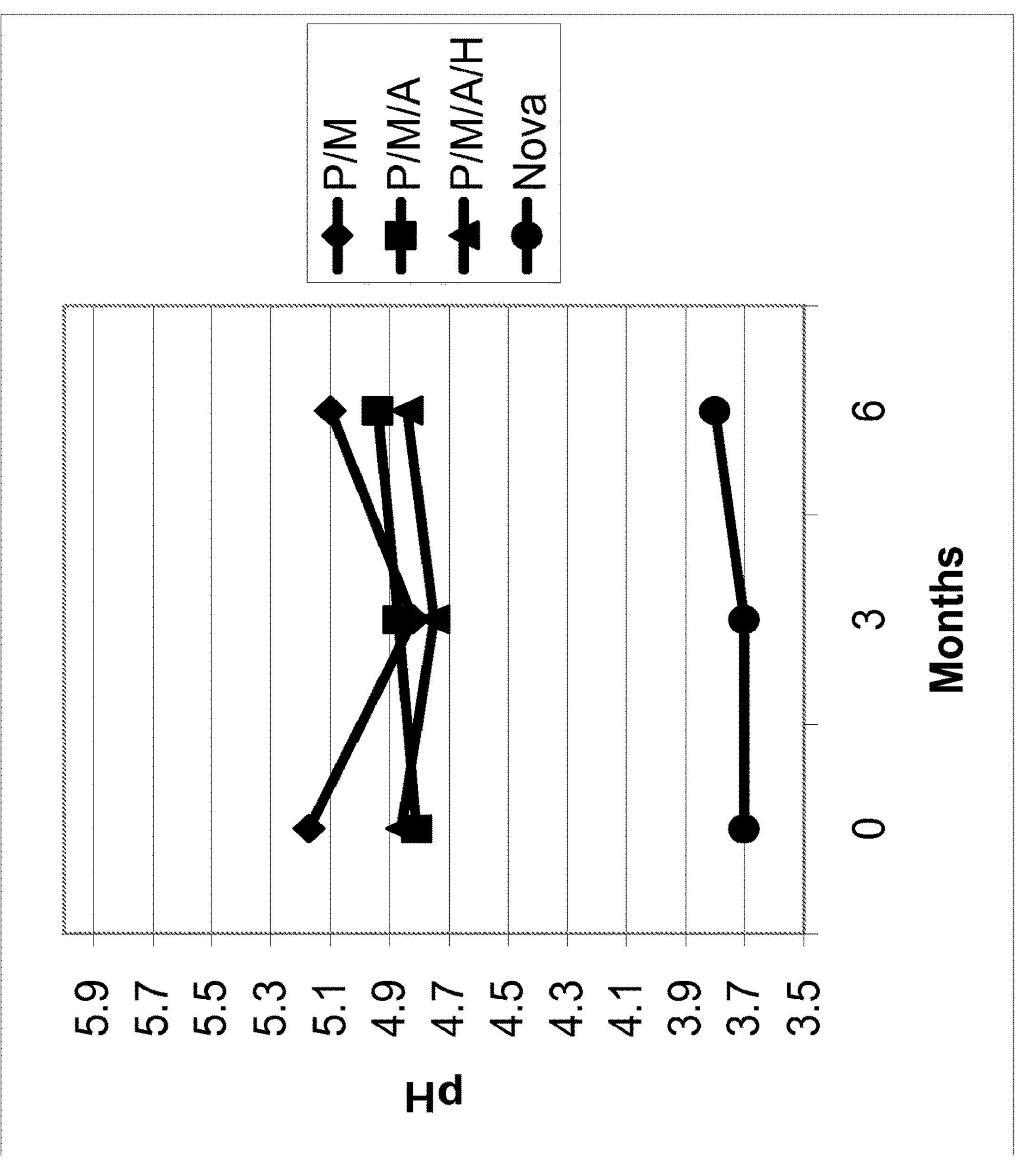
FIG. 3I is a line graph of pH of the phentolamine mesylate solution vs time for solutions stored at 2-8° C. containing (1) phentolamine mesylate and mannitol (abbreviated P/M); (2) phentolamine mesylate, mannitol and acetate buffer without HPMC (abbreviated P/M/A); (3) phentolamine mesylate, mannitol and acetate buffer with HPMC (abbreviated P/M/A/H); or (4) the Nova Formulation (identified as "Nova" in the figure legend).

FIG. 3G shows a line graph of percent of initial concentration of phentolamine mesylate remaining vs time for solutions stored at 2-8° C. FIG. 3H shows a line graph of area percent of phentolamine mesylate vs time for solutions stored at 2-8° C. FIG. 3I shows a line graph of pH of the phentolamine mesylate solution vs time for solutions stored at 2-8° C. In each of FIGS. 3G to 3I, the four lines in the graphs correspond to the four solutions tested: (1) a solution containing phentolamine mesylate and mannitol (abbreviated P/M); (2) a solution containing phentolamine mesylate, mannitol, and acetate buffer without IPMC (abbreviated P/M/A); (3) a solution containing phentolamine mesylate, mannitol and acetate buffer with IPMC (abbreviated P/M/A/H); and (4) the Nova Formulation (abbreviated "Nova").

As the data in Tables 4A-4F and FIGS. 3A-3I shows, both buffered formulations (with IPMC and without HPMC) are stable over time and demonstrate better stability than the conventional Nova formulation at 2-8° C., 25° C., and 40° C. Further, the pH of both buffered solutions declines only slightly over time.

In addition, a mildly buffered solution at pH of about 4.8 is closer to the physiologic pH of the eye than the strongly buffered Nova formulation (pH of about 3.7-3.8). The inventive formulations are also more comfortable because the mild buffer permits the rapid equilibration of pH in the cornea and does not promote stinging or watering of the eye upon application. In contrast, applying a more strongly buffered solution at a pH of about 3.7-3.8 would cause significant stinging and would not be comfortable for the subject receiving the solution.

Example 5—Stability Analysis of Phentolamine Mesylate Aqueous Ophthalmic Solutions Aqueous ophthalmic solutions containing mannitol (4% w/v), sodium acetate (3 mM) and either 0% w/v, 0.5% w/v, or 1% w/v phentolamine mesylate where stored for up to nine months at 5° C., 25° C., or 40° C. The pH of the solution and the amount of phentolamine mesylate in the solution was determined at the start of the experiment and at three-month intervals. Experimental results are shown in Tables 1 and 2 below. These results indicate that the phentolamine mesylate solution has good stability.

TABLE 1

PERCENTAGE OF INITIAL PHENTOLAMINE MESYLATE REMAINING UPON STORAGE.

| Storage Time | Percent of Initial Phentolamine Mesylate Remaining (%) Storage Temperature (° C.) | | | | | |
|---|---|---|---|---|---|---|
| | 5 | | 25 | | 40 | |
| | Phentolamine Mesylate Concentration (% w/v) | | | | | |
| (months) | 1.0 | 0.5 | 1.0 | 0.5 | 1.0 | 0.5 |
| 0 | 100 | 100 | 100 | 100 | 100 | 100 |
| 3 | 100 | 94 | 99 | 94 | 94 | 88 |
| 6 | 102 | 93 | 99 | 93 | 89 | 83 |
| 9 | 102 | 95 | 100 | 93 | N/A | N/A |

TABLE 2 pH OF PHENTOLAMINE MESYLATE SOLUTIONS UPON STORAGE.

| Storage Time | pH of the Solution Storage Temperature (° C.) | | | | | | | | |
|---|---|---|---|---|---|---|---|---|---|
| | 5 | | | 25 | | | 40 | | |
| | Phentolamine Mesylate Concentration (% w/v) | | | | | | | | |
| (months) | 1.0 | 0.5 | 0 | 1.0 | 0.5 | 0 | 1.0 | 0.5 | 0 |
| 0 | N/A | N/A | N/A | 4.8 | 4.9 | 4.9 | N/A | N/A | N/A |
| 3 | 4.8 | 4.9 | 5 | 4.8 | 4.9 | 5 | 4.8 | 4.9 | 5.1 |

TABLE 2-continued

| pH OF PHENTOLAMINE MESYLATE SOLUTIONS UPON STORAGE. | | | | | | | | | |
|---|---|---|---|---|---|---|---|---|---|
| | pH of the Solution Storage Temperature (° C.) | | | | | | | | |
| Storage Time | 5 | | | 25 | | | 40 | | |
| | Phentolamine Mesylate Concentration (% w/v) | | | | | | | | |
| (months) | 1.0 | 0.5 | 0 | 1.0 | 0.5 | 0 | 1.0 | 0.5 | 0 |
| 6 | 5.7 | 4.9 | 5 | 4.8 | 4.9 | 4.9 | 4.9 | 4.9 | 5 |
| 9 | 4.8 | 4.9 | 4.9 | 4.8 | 4.9 | 5 | N/A | N/A | N/A |

Example 6—Stability Analysis of Phentolamine Mesylate Aqueous Ophthalmic Solutions Aqueous ophthalmic solutions containing sodium acetate (3 mM), phentolamine mesylate (1 w/v), and either (i) mannitol (40 w/v), (ii) mannitol (2% w/v), (iii) glycerol (2 w/v), (iv) propylene glycol (2% w/v), or (v) mannitol (100 w/v) plus glycerol (1% w/v) were stored in low density polyethylene containers at 57° C. for 14 days. The solutions had a pH of 5.0 at the start of the experiment. The amount of phentolamine mesylate in the solution was determined at the start of the experiment and at two-day intervals after the start of the experiment. Experimental results are shown in Table 1 below.

TABLE 1

| PERCENTAGE OF INITIAL PHENTOLAMINE MESYLATE REMAINING UPON STORAGE. | | | | | |
|---|---|---|---|---|---|
| | Percentage of Initial of Phentolamine Mesylate (%) | | | | |
| Day | 4% (w/v) Mannitol | 2% (w/v) Mannitol | 2% (w/v) Glycerol | 2% (w/v) Propylene Glycol | 1% (w/v) Mannitol + 1% (w/v) Glycerol |
| 0 | 100.0 | 100.0 | 100.0 | 100.0 | 100.0 |
| 2 | 101.5 | 102.1 | 103.4 | 100.5 | 100.9 |
| 7 | 96.4 | 94.2 | 94.7 | 94.7 | 90.8 |
| 14 | 93.4 | 89.7 | 89.7 | 88.8 | 89.3 |

Aqueous ophthalmic solutions containing sodium acetate (10 mM), phentolamine mesylate (10% w/v), and either (i) mannitol (400 w/v), (ii) glycerol (250% w/v), or (iiii) propylene glycol (25% w/v) were stored glass containers at 60° C. for 14 days. The solutions had a pH of 3.5 at the start of the experiment. The amount of phentolamine mesylate in the solution was determined at the start of the experiment and then after 2 days, 7 days and 14 days after the start of the experiment. Experimental results are shown in Table 2 below.

TABLE 2

| PERCENTAGE OF INITIAL PHENTOLAMINE MESYLATE REMAINING UPON STORAGE. | | | |
|---|---|---|---|
| | Percentage of Initial of Phentolamine Mesylate (%) | | |
| Day | 4% (w/v) Mannitol Solution | 25% (w/v) Glycerol Solution | 25% (w/v) Propylene Glycol Solution |
| 0 | 100.0 | 100.0 | 100.0 |
| 2 | 98.0 | 97.6 | 102.5 |
| 7 | 100.0 | 95.2 | 95.8 |
| 14 | 92.9 | 91.3 | 89.8 |

Example 7—Stability Analysis of Phentolamine Mesylate Aqueous Ophthalmic Solutions Aqueous ophthalmic solutions containing mannitol (4% w/v), sodium acetate (3 mM) and either 0% w/v, 0.5% w/v, or 1% w/v phentolamine mesylate where stored for up to twenty-four months at (i) 5° C. at ambient relative humidity or (ii) 25° C. at 40% relative humidity. The ophthalmic solutions were analyzed for appearance, pH, osmolality, phentolamine mesylate potency, amount of phentolamine mesylate related substances, amount of particulates, weight loss, and sterility. Experimental results are described below, where the abbreviation "RH" refers to relative humidity. The experimental results show that the phentolamine mesylate solutions have good stability upon storage for twenty-four months at both (i) 5° C. at ambient relative humidity and (ii) 25° C. at 40% relative humidity.

A. Appearance

The appearance of the aqueous ophthalmic solutions and the appearance of the containers containing the aqueous ophthalmic solutions were analyzed at time points 1, 3, 6, 9, 12, 18, and 24 months after the start of the experiment. Except as noted below, the aqueous ophthalmic solutions were observed to be clear and colorless at each time point measured:

- For the 0.5% w/v phentolamine mesylate aqueous ophthalmic solution stored at 25° C. at 40% relative humidity, the solution was clear but slightly brown colored at time points 18 months and 24 months.
- For the 1.0% w/v phentolamine mesylate aqueous ophthalmic solution stored at 25° C. at 40% relative humidity, the solution was clear but contained a small brown fleck at the 12 month time point due to spillage on the neck of the bottle during filing operations that fell into the bottle during opening, and thus not indicative of product or container failure.

Except as noted below, the container was observed to be intact, with no evidence of leaking or crusting, at each time point measured:

- For the 1.0% w/v phentolamine mesylate aqueous ophthalmic solution stored at 25° C. at 40% relative humidity, the container was intact but brown crusting on the bottle was observed due to spillage on the neck of the bottle during prior filing operations.

B. Osmolality and pH

The osmolality and pH of the aqueous ophthalmic solutions is provided in Tables 1-3 below.

TABLE 1

| OSMOLALITY AND PH OF PLACEBO AQUEOUS OPHTHALMIC SOLUTION | | | |
|---|---|---|---|
| Storage Conditions | Pull Time (months) | pH | Osmolality (mOsm/kg) |
| 5° C./Ambient RH | Initial | 5.1 | 234 |
| | 1 | 4.9 | 229 |
| | 3 | 5.0 | 234 |
| | 6 | 5.0 | 233 |
| | 9 | 4.9 | 241 |
| | 12 | 5.0 | 238 |
| | 18 | 5.0 | 234 |
| | 24 | 5.0 | 234 |
| 25° C./40% RH | 1 | 5.0 | 234 |
| | 3 | 5.1 | 234 |
| | 6 | 4.9 | 239 |
| | 9 | 5.0 | 242 |
| | 12 | 4.9 | 236 |
| | 18 | 5.0 | 239 |
| | 24 | 5.0 | 239 |

TABLE 2

| OSMOLALITY AND PH OF 0.5% w/v PHENTOLAMINE MESYLATE AQUEOUS OPHTHALMIC SOLUTION | | | |
|---|---|---|---|
| Storage Conditions | Pull Time (months) | pH | Osmolality (mOsm/kg) |
| 5° C./Ambient RH | Initial | 5.1 | 259 |
| | 1 | 5.0 | 261 |
| | 3 | 4.9 | 256 |
| | 6 | 4.9 | 259 |
| | 9 | 4.9 | 264 |
| | 12 | 4.9 | 265 |
| | 18 | 4.9 | 259 |
| | 24 | 5.0 | 259 |
| 25° C./40% RH | 1 | 5.0 | 263 |
| | 3 | 4.9 | 263 |
| | 6 | 4.9 | 263 |
| | 9 | 4.9 | 274 |
| | 12 | 5.0 | 257 |
| | 18 | 4.9 | 264 |
| | 24 | 5.0 | 262 |

TABLE 3

| OSMOLALITY AND PH OF 1.0% w/v PHENTOLAMINE MESYLATE AQUEOUS OPHTHALMIC SOLUTION | | | |
|---|---|---|---|
| Storage Conditions | Pull Time (months) | pH | Osmolality (mOsm/kg) |
| 5° C./Ambient RH | Initial | 5.0 | 287 |
| | 1 | 4.9 | 286 |
| | 3 | 4.8 | 284 |
| | 6 | 4.7 | 286 |
| | 9 | 4.8 | 292 |
| | 12 | 4.8 | 287 |
| 25° C./40% RH | 1 | 4.9 | 284 |
| | 3 | 4.8 | 281 |
| | 6 | 4.8 | 285 |
| | 9 | 4.8 | 292 |
| | 12 | 4.9 | 284 |
| | 18 | 4.7 | 287 |
| | 24 | 4.9 | 285 |

C. Phentolamine Mesylate Potency

The phentolamine mesylate potency of the aqueous ophthalmic solutions is provided in Tables 4 and 5 below.

TABLE 4

| PHENTOLAMINE MESYLATE POTENCY OF 0.5% w/v PHENTOLAMINE MESYLATE AQUEOUS OPHTHALMIC SOLUTION | | |
|---|---|---|
| Storage Conditions | Pull Time (months) | Potency (% of Label Claim) |
| 5° C./Ambient RH | Initial | 104.0 |
| | 1 | 103.6 |
| | 3 | 101.5 |
| | 6 | 101.7 |
| | 9 | 102.9 |
| | 12 | 100.7 |
| | 18 | 102.6 |
| | 24 | 100.9 |
| 25° C./40% RH | 1 | 103.4 |
| | 3 | 101.4 |
| | 6 | 100.6 |
| | 9 | 100.8 |
| | 12 | 98.5 |
| | 18 | 98.7 |
| | 24 | 96.6 |

TABLE 5

| PHENTOLAMINE MESYLATE POTENCY OF 1.0% w/v PHENTOLAMINE MESYLATE AQUEOUS OPHTHALMIC SOLUTION | | |
|---|---|---|
| Storage Conditions | Pull Time (months) | Potency (%) |
| 5° C./Ambient RH | Initial | 102.7 |
| | 1 | 103.2 |
| | 3 | 101.9 |
| | 6 | 104.0 |
| | 9 | 103.6 |
| | 12 | 102.8 |
| 25° C./40% RH | 1 | 103.6 |
| | 3 | 100.9 |
| | 6 | 101.0 |
| | 9 | 101.8 |
| | 12 | 98.6 |
| | 18 | 96.6 |
| | 24 | 91.5 |

D. Amount of Phentolamine Mesylate Related Substances

The amount of phentolamine mesylate related substances identified by high-performance liquid chromatograph is provided in Tables 6 and 7 below.

TABLE 6

| AMOUNT OF PHENTOLAMINE MESYLATE RELATED SUBSTANCES IDENTIFIED IN 0.5% w/v PHENTOLAMINE MESYLATE AQUEOUS OPHTHALMIC SOLUTION | | |
|---|---|---|
| Storage Conditions | Pull Time (months) | Amount of Related Substances (Percent of Area Under Curve) |
| 5° C./Ambient RH | Initial | 0.09 |
| | 1 | 0.10 |
| | 3 | 0.21 |
| | 6 | 0.18 |
| | 9 | 0.26 |
| | 12 | 0.17 |
| | 18 | 0.17 |
| | 24 | 0.19 |

TABLE 6-continued

AMOUNT OF PHENTOLAMINE MESYLATE RELATED SUBSTANCES IDENTIFIED IN 0.5% w/v PHENTOLAMINE MESYLATE AQUEOUS OPHTHALMIC SOLUTION

| Storage Conditions | Pull Time (months) | Amount of Related Substances (Percent of Area Under Curve) |
|---|---|---|
| 25° C./40% RH | 1 | 0.29 |
| | 3 | 0.67 |
| | 6 | 1.10 |
| | 9 | 1.40 |
| | 12 | 1.92 |
| | 18 | 2.85 |
| | 24 | 3.64 |

TABLE 7

AMOUNT OF PHENTOLAMINE MESYLATE RELATED SUBSTANCES IDENTIFIED IN 1.0% w/v PHENTOLAMINE MESYLATE AQUEOUS OPHTHALMIC SOLUTION

| Storage Conditions | Pull Time (months) | Amount of Related Substances (Percent of Area Under Curve) |
|---|---|---|
| 5° C./Ambient RH | Initial | 0.14 |
| | 1 | 0.15 |
| | 3 | 0.22 |
| | 6 | 0.29 |
| | 9 | 0.27 |
| | 12 | 0.11 |
| 25° C./40% RH | 1 | 0.26 |
| | 3 | 0.51 |
| | 6 | 0.95 |
| | 9 | 0.95 |
| | 12 | 1.70 |
| | 18 | 2.15 |
| | 24 | 2.96 |

E. Amount of Particulates in Aqueous Ophthalmic Solutions

The amount of particulates in the aqueous ophthalmic solutions, as identified by high-performance liquid chromatograph, is provided in Tables 8-10 below.

TABLE 8

AMOUNT OF PARTICULATES IN PLACEBO AQUEOUS OPHTHALMIC SOLUTION

| Storage | Pull Time | Particle Count (particles/mL) | | |
|---|---|---|---|---|
| Conditions | (months) | ≥10 μm | ≥25 μm | ≥50 μm |
| 5° C./Ambient RH | Initial | 6 | 0 | 0 |
| | 6 | 48 | 0 | N/A |
| | 12 | 15 | 3 | N/A |
| | 24 | 1 | 0 | 0 |
| 25° C./40% RH | 6 | 1 | 0 | N/A |
| | 12 | 9 | 1 | N/A |
| | 24 | 1 | 1 | 1 |

TABLE 9

AMOUNT OF PARTICULATES IN 0.5% w/v PHENTOLAMINE MESYLATE AQUEOUS OPHTHALMIC SOLUTION

| Storage | Pull Time | Particle Count (particles/mL) | | |
|---|---|---|---|---|
| Conditions | (months) | ≥10 μm | ≥25 μm | ≥50 μm |
| 5° C./Ambient RH | Initial | 2 | 0 | 0 |
| | 12 | 13 | 1 | N/A |
| | 24 | 0 | 0 | 0 |
| 25° C./40% RH | 6 | 1 | 0 | N/A |
| | 12 | 42 | 4 | N/A |

TABLE 10

AMOUNT OF PARTICULATES IN 1.0% w/v PHENTOLAMINE MESYLATE AQUEOUS OPHTHALMIC SOLUTION

| Storage | Pull Time | Particle Count (particles/mL) | | |
|---|---|---|---|---|
| Conditions | (months) | ≥10 μm | ≥25 μm | ≥50 μm |
| 5° C./Ambient RH | Initial | 1 | 0 | 0 |
| | 12 | 21 | 2 | N/A |
| 25° C./40% RH | 6 | 3 | 0 | N/A |
| | 12 | 48 | 2 | N/A |
| | 24 | 3 | 2 | 2 |

F. Weight Loss for Aqueous Ophthalmic Solutions

Weight loss for the aqueous ophthalmic solutions (due to, for example, loss of water from the solution) was analyzed and results are provided in Tables 11-13 below. Five bottles of each type of aqueous ophthalmic solution (i.e., five bottles of placebo, five bottles of 0.5% w/v phentolamine mesylate, and five bottles of 1.000 w/v phentolamine mesylate) were analyzed.

TABLE 11

WEIGHT LOSS FOR PLACEBO AQUEOUS OPHTHALMIC SOLUTION

| Storage Conditions | Time Point (Months) | Weight Loss (% Lost from Initial) Bottle 1 | Bottle 2 | Bottle 3 | Bottle 4 | Bottle 5 |
|---|---|---|---|---|---|---|
| 5° C./Ambient RH | 1 | −0.1 | −0.1 | −0.1 | −0.1 | −0.1 |
| | 3 | 0.0 | −0.1 | −0.1 | −0.1 | −0.1 |
| | 6 | −0.1 | −0.1 | −0.1 | −0.1 | −0.1 |
| | 9 | 0.0 | 0.0 | 0.0 | 0.0 | 0.0 |
| | 12 | 0.1 | 0.0 | 0.0 | 0.0 | 0.0 |
| | 18 | −0.1 | −0.1 | −0.1 | −0.1 | −0.1 |
| | 24 | 0.0 | 0.0 | 0.0 | 0.0 | 0.0 |
| 25° C./40% RH | 1 | −0.2 | −0.2 | −0.2 | −0.2 | −0.2 |
| | 3 | 0.0 | 0.0 | 0.0 | 0.0 | 0.0 |
| | 6 | −0.1 | −0.1 | 0.0 | −0.1 | −0.1 |
| | 9 | 0.0 | 0.0 | −0.1 | 0.0 | −0.1 |
| | 12 | 0.0 | −0.1 | −0.1 | 0.0 | −0.1 |
| | 18 | −0.1 | −0.1 | −0.1 | −0.1 | −0.1 |
| | 24 | 0.0 | −0.1 | 0.0 | 0.0 | 0.0 |

TABLE 12

WEIGHT LOSS FOR 0.5% w/v PHENTOLAMINE MESYLATE AQUEOUS OPHTHALMIC SOLUTION

| Storage Conditions | Time Point (Months) | Weight Loss (% Lost from Initial) Bottle 1 | Bottle 2 | Bottle 3 | Bottle 4 | Bottle 5 |
|---|---|---|---|---|---|---|
| 5° C./Ambient RH | 1 | −0.1 | −0.1 | −0.1 | −0.3 | −0.2 |
| | 3 | −0.1 | −0.1 | −0.1 | −0.1 | −0.1 |
| | 6 | −0.1 | −0.1 | −0.1 | −0.1 | −0.1 |
| | 9 | 0.0 | 0.0 | 0.0 | 0.0 | 0.0 |
| | 12 | 0.0 | 0.0 | 0.0 | 0.0 | 0.0 |
| | 18 | −0.1 | −0.1 | −0.1 | −0.1 | −0.2 |
| | 24 | 0.0 | 0.0 | 0.0 | 0.0 | 0.0 |
| 25° C./40% RH | 1 | −0.2 | −0.1 | −0.2 | −0.1 | −0.1 |
| | 3 | −0.5 | −0.1 | −0.1 | 0.0 | −0.1 |
| | 6 | −0.9 | −0.1 | −0.1 | −0.1 | −0.1 |
| | 9 | −1.3 | 0.0 | 0.0 | 0.0 | 0.0 |
| | 12 | −1.9 | 0.0 | −0.1 | 0.0 | 0.0 |
| | 18 | −2.6 | −0.1 | −0.1 | −0.1 | −0.1 |
| | 24 | −2.9 | −0.1 | 0.0 | −0.1 | 0.0 |

TABLE 13

WEIGHT LOSS FOR 1.0% w/v PHENTOLAMINE MESYLATE AQUEOUS OPHTHALMIC SOLUTION

| Storage Conditions | Time Point (Months) | Weight Loss (% Lost from Initial) Bottle 1 | Bottle 2 | Bottle 3 | Bottle 4 | Bottle 5 |
|---|---|---|---|---|---|---|
| 5° C./Ambient RH | 1 | −0.2 | −0.3 | −0.1 | −0.1 | −0.1 |
| | 3 | 0.0 | 0.0 | 0.0 | 0.0 | 0.0 |
| | 6 | −0.1 | −0.1 | −0.1 | −0.1 | −0.1 |
| | 9 | 0.0 | 0.0 | 0.0 | 0.0 | 0.0 |
| | 12 | 0.1 | 0.0 | 0.0 | 0.0 | 0.0 |
| 25° C./40% RH | 1 | −0.1 | −0.1 | −0.1 | −0.4 | −0.3 |
| | 3 | 0.0 | 0.0 | 0.0 | 0.0 | 0.0 |
| | 6 | −0.1 | −0.1 | −0.1 | −0.1 | −0.1 |
| | 9 | 0.0 | 0.0 | 0.0 | 0.0 | 0.0 |
| | 12 | 0.0 | 0.0 | 0.0 | 0.0 | −0.1 |
| | 18 | −0.1 | −0.1 | −0.1 | −0.1 | −0.1 |
| | 24 | 0.0 | −0.1 | 0.0 | 0.0 | 0.0 |

G. Sterility of Aqueous Ophthalmic Solutions

Aqueous ophthalmic solutions were analyzed for sterility for up to 24 months at 5° C./ambient relative humidity and at 25° C./40% relative humidity, except for the 1.0% w/v phentolamine mesylate aqueous ophthalmic solutions which was stored at 5° C./ambient relative humidity which was analyzed for analyzed for only 12 months. No microbial growth was observed for any of the aqueous ophthalmic solutions over the duration of the test.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A method of making an aqueous ophthalmic solution, the method comprising combining:

a. phentolamine or a pharmaceutically acceptable salt thereof, wherein the phentolamine or a pharmaceutically acceptable salt thereof has a concentration of from about 0.1% (w/v) to about 4% (w/v) in the aqueous ophthalmic solution;

b. at least one polyol compound selected from the group consisting of mannitol, glycerol, propylene glycol, ethylene glycol, sorbitol, and xylitol;

c. at least one buffer, wherein said buffer has a concentration of from about 0.1 mM to about 10 mM in the aqueous ophthalmic solution;

d. water;

provided the aqueous ophthalmic solution does not contain any additional ingredient that is a chelating agent, and wherein the aqueous ophthalmic solution does not contain any additional ingredient that is a stabilizer.

2. The method of claim 1, further comprising adjusting the pH of the solution to a pH of about 4.0 to about 7.5.

3. The method of claim 2, wherein the solution comprises about 1% (w/v) of phentolamine mesylate; the buffer comprises sodium acetate; and about 4% (w/v) mannitol is present in the solution.

4. The method of claim 1, further comprising storing the aqueous ophthalmic solution at temperature in the range of 2-8° C.

5. The method of claim 2, further comprising storing the aqueous ophthalmic solution at temperature in the range of 2-8° C.

6. The method of claim 3, further comprising storing the aqueous ophthalmic solution at temperature in the range of 2-8° C.

7. A method of making an aqueous ophthalmic solution, the method consisting essentially of combining:

a. phentolamine or a pharmaceutically acceptable salt thereof, wherein the phentolamine or a pharmaceutically acceptable salt thereof has a concentration of from about 0.1% (w/v) to about 4% (w/v) in the aqueous ophthalmic solution;

b. at least one polyol compound selected from the group consisting of mannitol, glycerol, propylene glycol, ethylene glycol, sorbitol, and xylitol;

c. at least one buffer, wherein said buffer has a concentration of from about 0.1 mM to about 10 mM in the aqueous ophthalmic solution;

d. water;

provided the aqueous ophthalmic solution does not contain any additional ingredient that is a chelating agent; and wherein the aqueous ophthalmic solution does not contain any additional ingredient that is a stabilizer;

wherein optionally the pH of the solution is adjusted to a pH of about 4.0 to about 7.5, and optionally the aqueous ophthalmic solution is stored at a temperature in the range of 2-8° C.

8. The method of claim 7, wherein the pH of the solution is adjusted to a pH of about 4.0 to about 7.5.

9. The method of claim 8, wherein the solution contains about 1% (w/v) of phentolamine mesylate; the buffer comprises sodium acetate; and about 4% (w/v) mannitol is present in the solution.

10. The method of claim 7, wherein the aqueous ophthalmic solution is stored at a temperature in the range of 2-8° C.

11. The method of claim 8, wherein the aqueous ophthalmic solution is stored at a temperature in the range of 2-8° C.

12. The method of claim 9, wherein the aqueous ophthalmic solution is stored at a temperature in the range of 2-8° C.

13. A method of making an aqueous ophthalmic solution, the method consisting of combining:

a. phentolamine or a pharmaceutically acceptable salt thereof, wherein the phentolamine or a pharmaceutically acceptable salt thereof has a concentration of from about 0.1% (w/v) to about 4% (w/v) in the aqueous ophthalmic solution;

b. at least one polyol compound selected from the group consisting of mannitol, glycerol, propylene glycol, ethylene glycol, sorbitol, and xylitol;

c. at least one buffer, wherein said buffer has a concentration of from about 0.1 mM to about 10 mM in the aqueous ophthalmic solution;

d. water; and e. optionally one or more of a poly($C_{2-4}$ alkylene)glycol polymer, dextran, pharmaceutically acceptable carrier, cellulose agent, carbohydrate, alkali metal halide, alkaline earth metal halide, boric acid, cyclodextrin, dextrose, glycerin, urea, viscosity modifying agent, demulcent polymer, wetting agent, or water-miscible solvent;

wherein optionally the pH of the solution is adjusted to a pH of about 4.0 to about 7.5, and optionally the aqueous ophthalmic solution is stored at a temperature in the range of 2-8° C.

14. The method of claim 13, wherein the pH of the solution is adjusted to a pH of about 4.0 to about 7.5.

15. The method of claim 14, wherein the solution comprises about 1% (w/v) of phentolamine mesylate; the buffer comprises sodium acetate; and 4% (w/v) mannitol is present in the solution.

16. The method of claim 13, wherein the aqueous ophthalmic solution is stored at a temperature in the range of 2-8° C.

17. The method of claim 14, wherein the aqueous ophthalmic solution is stored at a temperature in the range of 2-8° C.

18. The method of claim 15, wherein the aqueous ophthalmic solution is stored at a temperature in the range of 2-8° C.

19. A method of making an aqueous ophthalmic solution, the method consisting essentially of combining:

a. phentolamine or a pharmaceutically acceptable salt thereof, wherein the phentolamine or a pharmaceutically acceptable salt thereof has a concentration of from about 0.1% (w/v) to about 4% (w/v) in the aqueous ophthalmic solution;

b. at least one polyol compound selected from the group consisting of mannitol, glycerol, propylene glycol, ethylene glycol, sorbitol, and xylitol;

c. at least one buffer, wherein said buffer has a concentration of from about 0.1 mM to about 10 mM in the aqueous ophthalmic solution;

d. water; and e. optionally one or more of an alkali metal halide or alkaline earth metal halide;

provided the aqueous ophthalmic solution does not contain any additional ingredient that is a chelating agent; and wherein the aqueous ophthalmic solution does not contain any additional ingredient that is a stabilizer;

wherein optionally the pH of the solution is adjusted to a pH of about 4.0 to about 7.5, and optionally the aqueous ophthalmic solution is stored at a temperature in the range of 2-8° C.

20. The method of claim 19, wherein the pH of the solution is adjusted to a pH of about 4.0 to about 7.5.

21. The method of claim 20, wherein the solution comprises about 1% (w/v) of phentolamine mesylate; the buffer comprises sodium acetate; and 4% (w/v) mannitol is present in the solution.

22. The method of claim 19, wherein the aqueous ophthalmic solution is stored at a temperature in the range of 2-8° C.

23. The method of claim 20, wherein the aqueous ophthalmic solution is stored at a temperature in the range of 2-8° C.

24. The method of claim 21, wherein the aqueous ophthalmic solution is stored at a temperature in the range of 2-8° C.

25. An aqueous ophthalmic solution made by the method of claim 13.

26. An aqueous ophthalmic solution made by the method of claim 14.

27. An aqueous ophthalmic solution made by the method of claim 15.

28. An aqueous ophthalmic solution made by the method of claim 19.

29. An aqueous ophthalmic solution made by the method of claim 20.

30. An aqueous ophthalmic solution made by the method of claim 21.

* * * * *